United States Patent
Laaksonen et al.

(10) Patent No.: US 11,842,498 B2
(45) Date of Patent: Dec. 12, 2023

(54) SYSTEMS AND METHODS FOR AUTOMATIC SEGMENTATION IN MEDICAL IMAGING WITH MULTIPLE ANATOMICAL STRUCTURE SEGMENTATION MODELS

(71) Applicant: Siemens Healthineers International AG, Steinhausen (CH)

(72) Inventors: Hannu Mikael Laaksonen, Espoo (FI); Janne Nord, Espoo (FI); Maria Isabel Cordero Marcos, Espoo (FI); Sami Petri Perttu, Helsinki (FI); Tomi Ruokola, Espoo (FI)

(73) Assignee: SIEMENS HEALTHINEERS INTERNATIONAL AG, Steinhausen (CH)

( * ) Notice: Subject to any disclaimer, the term of this patent is extended or adjusted under 35 U.S.C. 154(b) by 796 days.

(21) Appl. No.: 16/715,663

(22) Filed: Dec. 16, 2019

(65) Prior Publication Data

US 2021/0183070 A1   Jun. 17, 2021

(51) Int. Cl.
  *G06K 9/00*   (2022.01)
  *G06T 7/174*   (2017.01)
  (Continued)

(52) U.S. Cl.
  CPC ............ *G06T 7/174* (2017.01); *A61N 5/1038* (2013.01); *A61N 5/1048* (2013.01); *G06N 3/08* (2013.01); *G06N 5/022* (2013.01); *G06T 7/12* (2017.01); *G06T 7/149* (2017.01); *A61N 2005/1041* (2013.01); *A61N 2005/1074* (2013.01);
  (Continued)

(58) Field of Classification Search
  CPC ... G06T 7/174; G06T 7/11; G06T 7/12; G06T 2200/24; G06T 2207/20081; G06T 2207/20084; G06T 2207/20092; G06T 2207/20096; G06T 2207/20128; G06T 2207/20212; G06T 2207/30008; G06T 2207/30004; G06T 2207/30096; G06T 2207/30101; G06T 7/149; G06T 2207/20121; G06T 2207/20124; G06T 2207/20101; G06N 3/02; G06N 3/08; G06N 3/0445; G06N 5/02; G06N 5/022; A61B 1/00; A61B 1/00039; A61N 5/1038;
  (Continued)

(56) References Cited

U.S. PATENT DOCUMENTS 9,042,620 B2   5/2015   Kohlberger et al.
9,968,257 B1   5/2018   Burt
(Continued)

FOREIGN PATENT DOCUMENTS

WO   WO 2018/015414 A1   1/2018

OTHER PUBLICATIONS

Savadjiev et al., "Image-based biomarkers for solid tumor quantification", European Radiology, Springer International, Berlin, DE, vol. 29, No. 10, Apr. 8, 2019, pp. 5431-5440.
(Continued)

*Primary Examiner* — Duy M Dang
(74) *Attorney, Agent, or Firm* — Potomac Law Group, PLLC

(57) ABSTRACT

Systems and methods for anatomical structure segmentation in medical images using multiple anatomical structures, instructions and segmentation models.

20 Claims, 15 Drawing Sheets

(51) Int. Cl.
*G06T 7/149* (2017.01)
*A61N 5/10* (2006.01)
*G06N 3/08* (2023.01)
*G06N 5/022* (2023.01)
*G06T 7/12* (2017.01)

(52) U.S. Cl.
CPC .............................. *G06T 2200/24* (2013.01); *G06T 2207/20084* (2013.01); *G06T 2207/20092* (2013.01); *G06T 2207/20096* (2013.01); *G06T 2207/20121* (2013.01); *G06T 2207/20124* (2013.01); *G06T 2207/20128* (2013.01); *G06T 2207/20212* (2013.01); *G06T 2207/30008* (2013.01); *G06T 2207/30096* (2013.01); *G06T 2207/30101* (2013.01)

(58) Field of Classification Search
CPC .......... A61N 5/1048; A61N 2005/1041; A61N 2005/1074
See application file for complete search history.

(56) References Cited

U.S. PATENT DOCUMENTS

| | | | |
|---|---|---|---|
| 10,032,281 | B1 | 7/2018 | Ghesu et al. |
| 10,340,046 | B2 | 7/2019 | Baker |
| 10,453,200 | B2 | 10/2019 | Mukherjee et al. |
| 2017/0213339 | A1 | 7/2017 | Hibbard et al. |
| 2019/0205606 | A1* | 7/2019 | Zhou .................... G06N 3/0445 |
| 2019/0251694 | A1 | 8/2019 | Han et al. |
| 2020/0104695 | A1 | 4/2020 | Laaksonen et al. |

OTHER PUBLICATIONS

International Search Report and Written Opinion dated Mar. 12, 2021, in International Application No. PCT/EP2020/085121.

Delpon et al., "Comparison of Automated Atlas-Based Segmentation Software for Postoperative Prostate Cancer Radiotherapy," Frontiers in Oncology, Aug. 2016, vol. 6, Article 178.

Tong et al., "Fully automatic multi-organ segmentation for head and neck cancer radiotherapy using shape representation model constrained fully convolutional neural networks," Med. Phys. vol. 45 (10), Oct. 2018, American Association of Physicists in Medicine.

Apte et al., "Library of model implementations for sharing deep-learning image segmentation and outcomes models," bioRxiv preprint first posted online Sep. 19, 2019; doi: http://dx.doi.org/10.1101/773929.

Wang et al., "Automatic multi-organ segmentation using fast model based level set method and hierarchical shape priors," Proceedings of the VISCERAL Organ Segmentation and Landmark Detection Benchmark at the 2014 IEEE International Symposium on Biomedical Imaging (ISBI), Beijing, China, May 1, 2014.

McCoy et al., "Convolutional Neural Network-Based Automated Segmentation of the Spinal Cord and Contusion Injury: Deep Learning Biomarker Correlates of Motor Impairment in Acute Spinal Cord Injury," AJNR Am J Neuroradiol 40:737-44, Apr. 2019, www.ajnr.org.

Ahmad et al., "Deep Belief Network Modelling for Automatic Liver Segmentation," DOI 10.1109/ACCESS.2019.2896961, IEEE Access.

International Search Report and Written Opinion dated May 17, 2022, in International Application No. PCT/EP2020/085121.

* cited by examiner

SYSTEMS AND METHODS FOR AUTOMATIC SEGMENTATION IN MEDICAL IMAGING WITH MULTIPLE ANATOMICAL STRUCTURE SEGMENTATION MODELS

FIELD

The present disclosure relates generally to medical imaging, and more particularly, to systems and methods for anatomical structure segmentation in medical images using multiple anatomical structures, instructions and segmentation models.

BACKGROUND

Radiotherapy is an important tool for the treatment of cancerous tumors in patients. Unfortunately, ionizing radiation applied to treat the patient does not inherently discriminate between tumors and proximal healthy structures (e.g., organs-at-risk). Administration of the ionizing radiation thus must be carefully tailored to restrict the applied radiation to the target (i.e., tumor) while avoiding unnecessary irradiation of surrounding anatomy, the goal being to deliver a lethal radiation dose to the tumor while maintaining an acceptable dosage to the proximal structures.

As part of the radiotherapy planning process, medical images of the tumor and surrounding anatomy are obtained. The medical images can serve as a basis for simulations of the radiation treatment and can be used to plan various aspects of the therapy, including but not limited to, beam geometry and location, radiation energy, and dosage. The medical images are typically processed to delineate target regions (e.g., pixels or voxels where a tumor or other regions desired to be irradiated are imaged) and separate surrounding structures (e.g., pixels or voxels where an organ-at-risk (OAR) or other anatomical structure to avoid being irradiated is imaged). This delineation, termed contouring or segmenting, involves defining a respective border defining outlines of the different anatomical structures in the image. However, if anatomical structures are improperly contoured in the images, this could result in insufficient irradiation of the target and/or undesirable irradiation of surrounding structures.

Manual contouring of structures in medical images can not only be a time-consuming phase in the radiotherapy planning process, but it may also introduce inconsistencies due to both the inter-patient and inter-observer variabilities. To address this issue, automatic segmentation models have been proposed. Existing automatic segmentation methods can be broadly categorized as atlas based segmentation methods, statistical shape or appearance based segmentation methods, machine learning segmentation methods, or deep learning based segmentation methods. Although these automatic segmentation methods have shown great promise in medical image segmentation, they each have their own advantages and drawbacks, especially for multi-structure segmentation, where delineating the border of each anatomical structure can be difficult due to limited resolution and lack of contrast between closely attached anatomical structures.

For example, the atlas based segmentation methods build a library of OARs from manual segmentation and then extrapolate the library to a new patient via image registration. Once an atlas is established on previously delineated patients, atlas methods can perform non-supervised segmentation on a new patient. The atlas based segmentation methods, however, are sensitive to atlas selection and strongly depend on the registration accuracy, and they usually require one or a number of "standard" patients with known partitioning (i.e., known atlas). Also, if many atlases are used, atlas based segmentation may be slow to run.

Shape or appearance statistical model-based segmentation methods delineate organs by restricting the final segmentation results to anatomically plausible shapes described by statistical models. Thus, the shape or appearance statistical model-based segmentation methods are limited to the shape representation capacities of the statistical models. Moreover, the statistical shape models may not be sufficient to estimate shapes if the connection between organs is too large.

Machine learning segmentation methods generally involve extracting feature vectors from images, such as for every voxel, etc., that may be used as input to a machine learning model, such as random forests, probabilistic models, and dictionary learning for segmentation, for example, that classify which class each voxel belongs to. Machine learning segmentation methods generally require careful initialization, usually by a human expert, and usually do not make use of complete image data and require additional constraints.

Deep learning based segmentation methods, on the other hand, utilize many layers or stages of nonlinear data processing for feature learning as well as pattern analysis and/or classification. Deep learning generally refers to a hierarchy of layers of nonlinear data processing that include an input layer, an output layer, and multiple "hidden" layers between the input and output layers. These layers may be trained to extract feature(s) from an input and classify the feature(s) to produce an output. Deep learning based segmentation methods, although superior to the other methods, have their own drawbacks, however. Generally, deep learning segmentation methods involve a training phase and an inference phase, as shown in FIG. 17. In the training phase, a deep neural network (DNN) model uses training data sets of medical images to generate a particular output. For example, the training data set can include 2-D or 3-D images with ground truth contours for the anatomical structures imaged by the different pixels or voxels. During the inference phase, the trained DNN model operates on medical image(s) of a patient to automatically process features of the medical image(s). Since deep learning based segmentation methods are strongly dependent on the data set they train on, these segmentation models have their own list of structures/organs that they create when applied. As such, a single deep learning (DNN) segmentation model may not contain all the desired structures to contour, or the model might fail to contour properly a particular structure, even though it properly contours others.

Thus, each of the different segmentation methods have their own advantages and drawbacks. Further, a single segmentation method may not work to automatically contour a plurality of anatomical structures.

Embodiments of the disclosed subject matter may address one or more of the above-noted problems and disadvantages, among other things.

SUMMARY

Embodiments of the disclosed subject matter provide a platform and supported graphical user interface (GUI) decision-making tools for use by a user (e.g., medical personnel, for example) to aid in the process of automatic multi-structure segmentation by allowing the user to access a database containing different segmentation models of different segmentation protocols (i.e., models of DNN, machine learning, shape or appearance and atlas-based protocols, for example), to select all or a subset of segmentation models that are applicable and/or are better for contouring a particular anatomical structure, and to selectively combine the results of the different segmentation model outcomes.

Embodiments of the disclosed subject matter provide a user with the ability to select and apply different segmentation models to contour each of the desired anatomical structures (i.e., organs, for example), combine results of the different segmentation outcomes, and apply alternative or additional imaging modalities for different anatomical structures.

Embodiments of the disclosed subject matter provide a platform and supported graphical user interface decision-making tools to allow a user to automatically segment a plurality of anatomical structures using multiple segmentation models.

Embodiments of the disclosed subject matter also provide a network-based system and method by which a library of different image segmentation models can be accessed and applied to automatically contour one or more selected anatomical structures, and to selectively combine the generated contours.

In one or more embodiments, the system comprises a processor configured to access, via the network, the library of different image segmentation models, to select and apply all or a subset of the image segmentation models to be used to contour one or more anatomical structures selected by a user via a user interface, and to combine results of different segmentation model outcomes to generate the desired contours.

Embodiments of the disclosed subject matter further provide a memory having instructions thereon, wherein when executed, the instructions cause the processor to access a database including one or more medical images associated with a patient; access a database including the library of different image segmentation models; and, upon a request by the user via the user interface, to contour one or more anatomical structures on one or more of the medical images.

In embodiments, the processor is further configured to determine which ones of the segmentation models in the database support segmentation of at least one of the one or more anatomical structures desired to be contoured, display to the user, on a selection screen, a list of the image segmentation models determined to support segmentation of one or more of the desired anatomical structures, and a list of the anatomical structures that each of the determined segmentation models supports, and, for each anatomical structure desired to be contoured, allow the user to select one or more segmentation models from the displayed list to be used.

In one or more embodiments, the processor is further configured to prompt the application of the selected segmentation models to generate corresponding contours for the desired anatomical structures, and to allow for the display of the generated contours on the one or more images for user review.

Embodiments of the disclosed subject matter further provide tools to allow the user to accept or reject any of the generated contours, to allow the user to combine the contours obtained for the same anatomical structure using different segmentation models, to allow the user to combine the contours obtained for different anatomical structures using different segmentation models, and to allow the user to select a different subset of segmentation models from the library to generate different contours for any of the rejected contours.

Embodiments of the disclosed subject matter further provide for an automatic segmentation method, comprising: inputting by a user via a user interface a list of anatomical structures desired to be contoured; automatically generating and displaying on a selection screen of the user interface a list of available segmentation models suitable to contour at least one of the desired anatomical structures, and a list of anatomical structures each available segmentation model supports; for each desired anatomical structure, allowing the user to select one or more of the displayed segmentation models to be used for contouring; applying the selected segmentation models; and displaying the segmentation results to the user for review.

Embodiments further provide methods that allow the user to return to the selection screen and select a different set of segmentation models for contouring, upon determination by the user that one or more of the segmentation results are not acceptable.

Embodiments further provide a method wherein the automatic generation of the list of suitable segmentation models includes: accessing via the network a database including a plurality of automatic segmentation models and corresponding anatomical structures each of the segmentation models supports; determining which ones of the automatic segmentation models in the database support segmentation of at least one of the desired anatomical structures; and selecting for display to the user each of the segmentation models from the database that support segmentation of at least one of the desired anatomical structures.

In one or more embodiments, the applying of the selected segmentation models may include: accessing via the network the selected segmentation models; and, for each desired anatomical structure, applying the selected one or more segmentation models to generate one or more contours.

In one or more embodiments, the segmentation models can be applied in consecutive or simultaneous fashion.

Embodiments further provide allowing the user to combine the segmentation results.

In one or more embodiments the combining may be done on a weighted basis, and/or using Boolean operations, and/or manually.

Embodiments further provide for the further processing of the generated contours prior to display to the user.

In one or more embodiments the further processing may include automatically modifying the generated contours by modifying the margins of the anatomical structures, and/or automatically rejecting specific contours, and/or modifying the generated contours.

Embodiments of the disclosed subject matter also provide a non-transitory computer-readable storage medium and a computer processing system. The non-transitory computer-readable storage medium can have embodied thereon a sequence of programmed instructions. The computer processing system can be configured to execute the sequence of programmed instructions embodied on the computer-readable storage medium to cause the computer processing system to process one or more medical images of a patient using a plurality of different segmentation models from a library of segmentation models to generate one or more contours of anatomical structures in the one or more medical images of the patient.

Embodiments of the disclosed subject matter further provide a system comprising a radiotherapy device configured to deliver radiation treatment to a patient, wherein a processor is further configured to control the radiotherapy device to irradiate the patient according to a treatment plan based at least on the one or more medical images of the patient and contours generated according to any of the systems and methods disclosed herein.

Objects and advantages of embodiments of the disclosed subject matter will become apparent from the following description when considered in conjunction with the accompanying drawings.

BRIEF DESCRIPTION OF DRAWINGS

Embodiments will hereinafter be described with reference to the accompanying drawings, which have not necessarily been drawn to scale. These drawings are for illustration purposes only and are not intended to limit the scope of the present disclosure in any way. Where applicable, some features may not be illustrated to assist in the illustration and description of underlying features. Throughout the figures, like reference numerals denote like elements. As used herein, various embodiments can mean one, some, or all embodiments.

DETAILED DESCRIPTION

Figure 1:
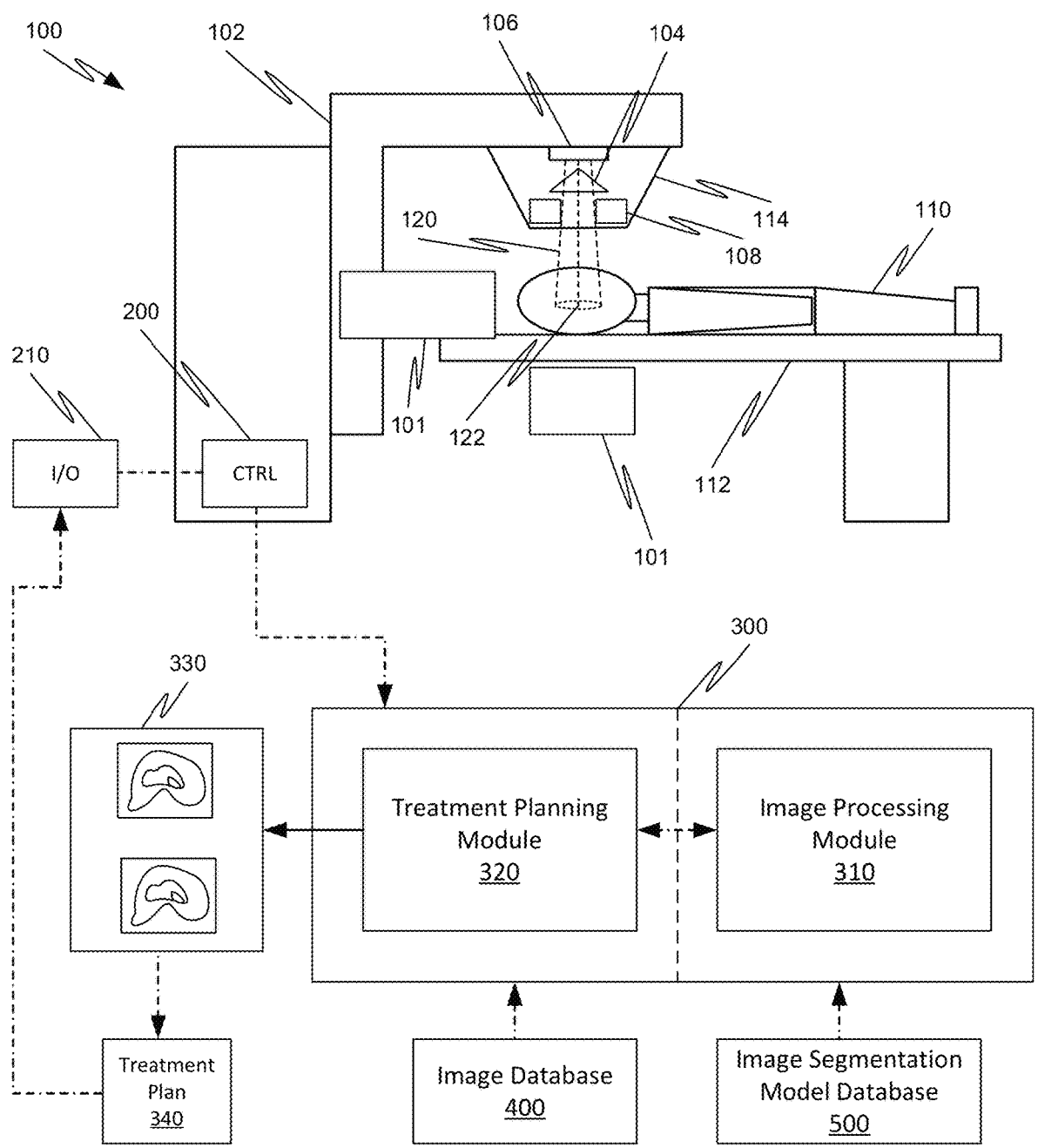
FIG. 1 is a simplified schematic diagram illustrating an example process flow for radiotherapy treatment and aspects of a medical image processing and radiotherapy systems, according to various embodiments of the disclosed subject matter.

FIG. 1 is a schematic diagram illustrating a process flow for a radiotherapy treatment. For example, a treatment planning system 300 can be used to generate treatment plans 340 for the radiation therapy system 100, based on image data obtained for a patient 110 using one or more of computed tomography (CT), cone beam computed tomography (CBCT), positron emission tomography (PET), magnetic resonance imaging (MRI), single photon emission computed tomography (SPECT) or any other imaging methodology. For example, when CT or MRI is used, image data may include a series of two-dimensional (2D) images or slices (i.e., planning images), each representing a cross-sectional view of the patient's anatomy, or may include volumetric or three-dimensional (3D) images of the patient 110, or may include a time series of 2D or 3D images of the patient 110. The image data can be saved in an image database/storing device 401 and/or a network accessible image database 400 shown in FIG. 3, for example.

Figure 2:
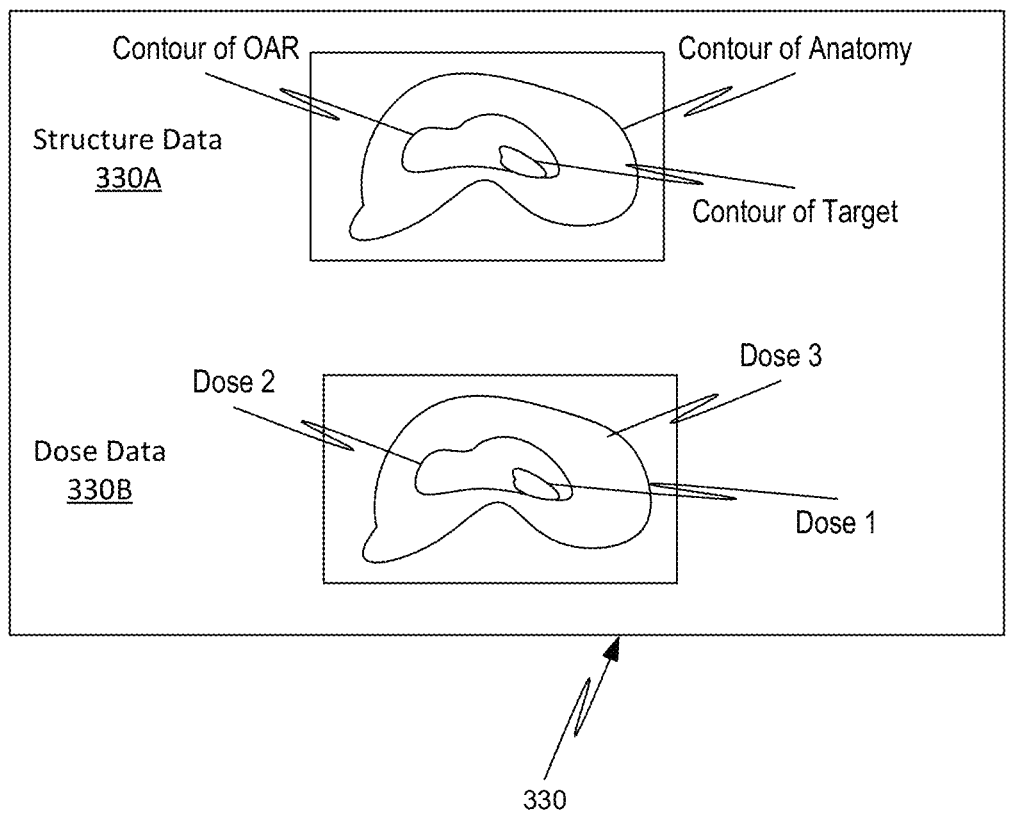
FIG. 2 is a simplified schematic diagram of structure and dose data obtained during radiotherapy treatment processing, according to various embodiments of the disclosed subject matter.

The treatment planning system 300 performs any suitable number of treatment planning tasks or steps, such as segmentation, dose prediction, projection data prediction, treatment plan generation, etc. The treatment planning system 300 may include an image processing module 310 configured to perform segmentation to generate structure data 330A identifying various anatomical structures, such as, but not limited to, the malignant tumor (i.e., the target), and any organs-at-risk (OAR), as shown in FIG. 2, for example. The structure data 330A may also identify other anatomical structures, such as other organs, tissues, bones, blood vessels, etc. The structure data 330A may also include any suitable data relating to the contour, shape, size, and location of a patient's anatomy, the malignant tumor (i.e., the target), any organs-at-risk (OAR), and any other anatomical structures.

For multi-structure segmentation, contours of the different anatomical structures can be generated on one or more of the initial planning images manually, semi-automatically or automatically. In an automatic segmentation process, the planning images are automatically segmented to delineate the malignant tumor that is to be the target of the irradiation and any other desired anatomical structures, such as different organs, OARs, bones, blood-vessels, tissues, etc.

Once the desired anatomical structures are segmented, a treatment plan is generated using a treatment planning module 320, by which dose data 330B, as shown in FIG. 2, is determined specifying the radiation dose to be delivered to the target and any other anatomical structure desired to be irradiated, and specifying the maximum allowable radiation dose that is allowed to be delivered to other anatomical structures, such as the OARs, for example. The treatment plan 340 therefore contains information 330 relating to the structure data 330A and dose data 330B. The treatment plan 340 may also contain any other additional data, such as prescription, disease staging, biologic or radiomic data, genetic data, assay data, past treatment or medical history, or any combination thereof. The treatment plan 340 may also take into consideration constraints imposed on the treatment process by the radiation therapy system 100 used for delivering the radiation to the patient 110.

An exemplary radiation therapy system 100 that can be used to deliver radiation in accordance with the treatment plan 340 generated by the radiation treatment planning system 300 is also show in FIG. 1. The radiation therapy system 100 can provide radiation to a patient 110 positioned on a treatment couch 112 and can allow for the implementation of various radiation dose verification protocols. The radiation therapy can include photon-based radiation therapy, particle therapy, electron beam therapy, or any other type of treatment therapy.

Alternatively, the treatment planning system 300 can be used to generate data 330 for a treatment plan 340 used in systems other than external radiation therapy, such as, but not limited to brachytherapy, cryotherapy, microwave ablation, radiofrequency ablation, interventional medicine, embolization, etc.

In an embodiment, the radiation therapy system 100 can include a radiation treatment device 101 such as, but not limited to, a LINAC operable to generate one or more beams of megavolt (MV) X-ray radiation for treatment. The LINAC may also be operable to generate one or more beams of kilovolt (kV) X-ray radiation, for example, for patient imaging. The system 100 has a gantry 102 supporting a radiation treatment head 114 with one or more radiation sources 106 and various beam modulation elements, such as, but not limited to, flattening filter 104 and collimating components 108. The collimating components 108 can include, for example, a multi-leaf collimator (MLC), upper and lower jaws, and/or other collimating elements. The collimating components 108 and/or the flattening filter 104 can be positioned within the radiation beam path by respective actuators (not shown), which can be controlled by controller 200.

The gantry 102 can be a ring gantry (i.e., it extends through a full 360° arc to create a complete ring or circle), but other types of mounting arrangements may also be employed. For example, a static beam, or a C-type, partial ring gantry, or robotic arm can be used. Any other framework capable of positioning the treatment head 114 at various rotational and/or axial positions relative to the patient 110 may also be used.

In an embodiment, the radiation therapy device is a MV energy intensity modulated radiation therapy (IMRT) device. The intensity profiles in such a system are tailored to the treatment requirements of the individual patient. The IMRT fields are delivered with MLC 108, which can be a computer-controlled mechanical beam shaping device attached to the head 114 and includes an assembly of metal fingers or leaves. For each beam direction, the optimized intensity profile is realized by sequential delivery of various subfields with optimized shapes and weights. From one subfield to the next, the leaves may move with the radiation beam on (i.e., dynamic multi-leaf collimation (DMLC)) or with the radiation beam off (i.e., segmented multi-leaf collimation (SMLC)).

Alternatively, or additionally, the radiation therapy device 101 can be a tomotherapy device, a helical tomotherapy device, or a simplified intensity modulated arc therapy (SIMAT) device, a volumetric modulated arc therapy (VMAT) device, or a volumetric high-definition (or hyper-arc) therapy (HDRT). In effect, any type of IMRT device can be employed as the radiation therapy device 101 of system 100, and can also include an on-board volumetric imaging, which can be used to generate in-treatment image data generated during a treatment session.

Each type of radiation therapy device can be accompanied by a corresponding radiation plan and radiation delivery procedure.

The controller 200, which can be, but is not limited to, a graphics processing unit (GPU), can include a computer with appropriate hardware such as a processor, and an operating system for running various software programs and/or communication applications. The controller 200 can include software programs that operate to communicate with the radiation therapy device 101, which software programs are operable to receive data from external software programs and hardware. The computer can also include any suitable input/output (I/O) devices 210, which can be adapted to allow communication between controller 200 and a user of the radiation therapy system 100, e.g., medical personnel. For example, the controller 200 can be provided with I/O interfaces, consoles, storage devices, memory, keyboard, mouse, monitor, printers, scanner, as well as a departmental information system (DIS) such as a communication and management interface (DICOM) for storing and transmitting medical imaging information and related data and enabling the integration of medical imaging devices such as scanners, servers, workstations, printers, network hardware, etc.

Figure 3:
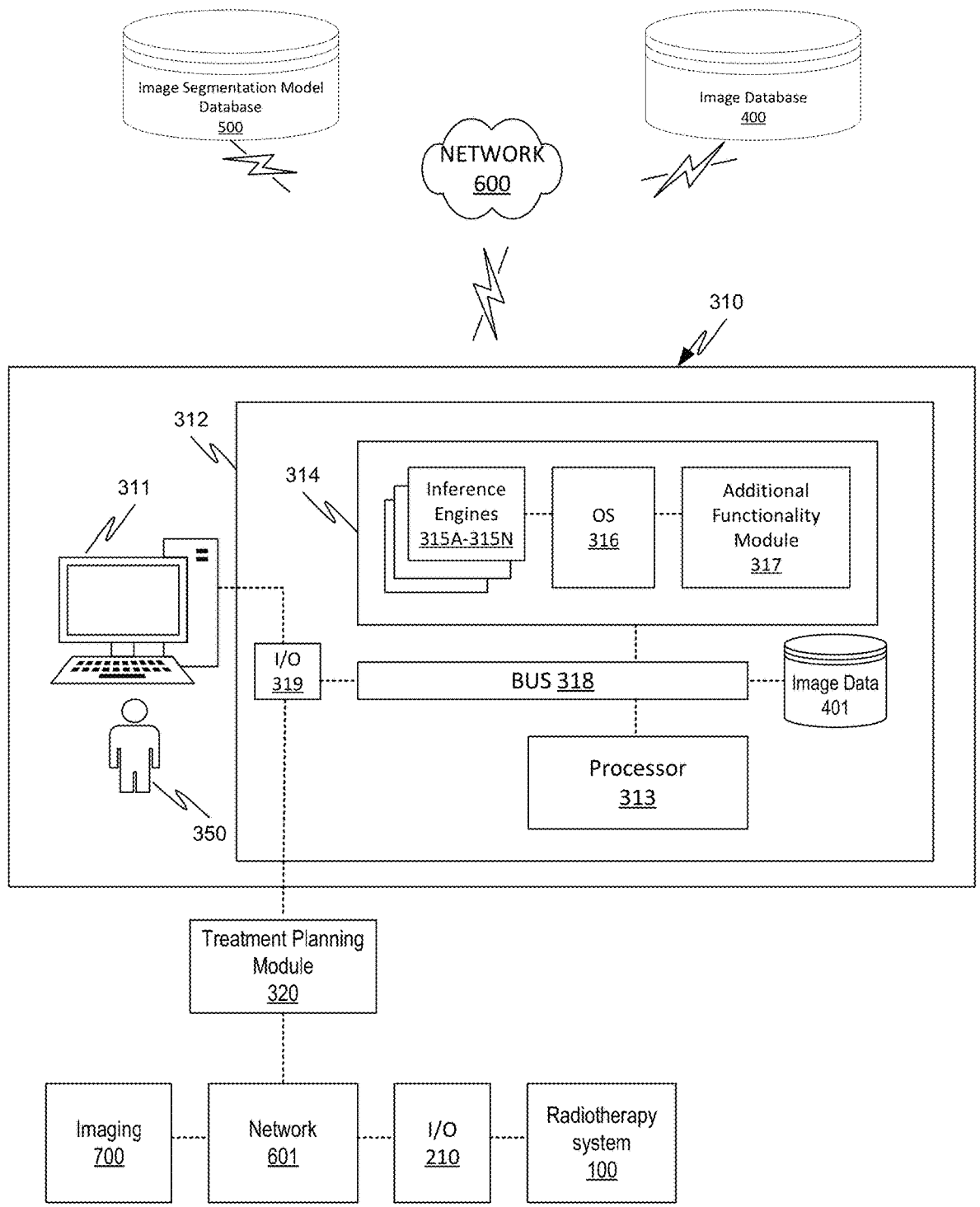
FIG. 3 is a simplified schematic diagram illustrating aspects of a medical image processing, according to various embodiments of the disclosed subject matter.

Alternatively, or additionally, the I/O devices 210 can provide access to one or more networks, such as networks 600 and 601 shown in FIG. 3, for example, for transmitting data between controller 200 and remote systems. For example, the controller 200 can be networked via I/O 210 with other computers and radiation therapy systems. The radiation therapy system 100, the radiation treatment device 101, and the controller 200 can communicate with the networks 600, 601 as well as databases and servers, for example, a dose calculation server (e.g., distributed dose calculation framework) and the treatment planning system 300. The controller 200 may also be configured to transfer medical image related data between different pieces of medical equipment.

The system 100 can also include a plurality of modules containing programmed instructions (e.g., as part of controller 200, or as separate modules within system 100, or integrated into other components of system 100), which instructions cause system 100 to perform different functions related to adaptive radiation therapy or other radiation treatment. For example, the system 100 can include a treatment plan module operable to generate the treatment plan for the patient 110 based on a plurality of data input to the system by the medical personnel, a patient positioning module operable to position and align the patient 110 with respect to a desired location, such as the isocenter of the gantry, for a particular radiation therapy treatment, an image acquiring module operable to instruct the radiation therapy system and/or the imaging device to acquire images of the patient 110 prior to the radiation therapy treatment (i.e., pre-treatment/reference images used for treatment planning and patient positioning) and/or during the radiation therapy treatment (i.e., in-treatment session images), and to instruct the radiation therapy system 100 and/or the imaging device 101 or other imaging devices or systems to acquire images of the patient 110.

The system 100 can further include a radiation dose prediction module operable to predict a dose to be delivered to the patient 110 before commencement of the radiation treatment therapy, a dose calculation module operable to calculate the actual dose delivered to the patient 110 during radiation therapy treatment, a treatment delivery module operable to instruct the radiation therapy device 100 to deliver the treatment plan to the patient 110, a correlation module operable to correlate the planning images with the in-treatment images obtained during radiation therapy, a computation module operable to reconstruct three-dimensional target volumes from in-treatment images, an analysis module operable to compute displacement measurements, and a feedback module operable to instruct the controller in real-time to stop radiation therapy based on a comparison of the calculated displacement with a predetermined threshold value (range).

The system 100 can further include one or more contour generation modules operable to generate contours of target volumes and other structures in pre-treatment (planning, reference) and in-treatment (treatment session) images, an image registration module operable to register pre-treatment images with subsequent in-treatment images, a dose calculation module operable to calculate accumulated dose, a contour propagation module operable to propagate a contour from one image to another, a contour verification module operable to verify a generated contour, a registration deformation vector field generation module operable to determine deformation vector fields (DVFs) as a result of an image deformation process. The system 100 can further include modules for electron density map generation, isodose distribution generation, does volume histogram (DVH) generation, image synchronization, image display, treatment plan generation, treatment plan optimization, automatic optimization parameter generation, updating and selection, and adaptive directives and treatment information transfer. The modules can be written in the C or C++ programming language, for example. Computer program code for carrying out operations as described herein may be written in any programming language, for example, C or C++ programming language.

An exemplary image processing module 310 of a treatment planning system 300 is illustrated in FIG. 3. Image processing module 310 may include, for example, a computer system 312 that can implement one or more aspects of the process of FIGS. 6-16. Although shown as a single module 310, the functionality of module 310 can be implemented as a distributed system or otherwise. Moreover, although illustrated separately, the image processing module 310 and the treatment planning module 320 (FIG. 1) may be integrated together, for example, as a single module with both image processing and treatment planning functionality provided by memory 314, as separate parts of a common computer system 312, or as separate parts of a common system (e.g., a central or distributed processing system operating on a remote server).

The computer system 312 can include a bus 318 or other mechanism for communicating information between components. The computer system 312 can also include a processor 313, for example, a general or specific purpose processor (e.g., graphics processing unit (GPU)), coupled to bus 318. The processor 313 can be a processor of a cloud-based system, and/or a processor of one or more network or Internet host servers. The computer system 312 can include an input/output module 319, for example, a communication device such as network interface cards that provide access to network 600 to communicate with an image database 400 and image segmentation model database 500, and with network 601 to communicate with the radiation therapy system 100, and/or input/output ports that allow a user 350 to interact with the computer system 312, for example via user input devices including a mouse, keyboard, display, etc., such as an interactive graphical user interface (GUI) 311.

The GUI 311 can include, but is not limited to, user-selectable and/or user-adjustable graphical controls, such as, but not limited to, slider bars, option buttons, text bars, drop-down boxes, windows, animations, and/or any other GUI components for selecting and/or adjusting a digital presentation of 3D and/or 2D images and/or image slices, and/or contours of anatomical structures caused to be displayed by the processor 313, and/or lists of available segmentation models and supported anatomical structures caused to be displayed by the processor 313 or the computer system 312, or otherwise. The GUI 311 is configured to allow the user 350 to input data, manipulate input and output data, and make any edits to the data, to the generated contours, and to the displayed output. A user 350 can interact with computer system 312 directly or remotely through networks 600, 601 or via any other methods.

The computer system 312 can also include a memory 314 that stores information and instructions to be executed by processor 313. The memory 314 can be comprised of any combination of random access memory (RAM), read only memory (ROM), static storage such as a magnetic or optical disk, or any other type of computer readable media. For example, computer readable media may be any available media that can be accessed by processor 313 and can include both volatile and nonvolatile media, removable and non-removable media, and communication media. Communication media may include computer readable instructions, data structures, program modules or other data in a modulated data signal such as a carrier wave or other transport mechanism and includes any information delivery media.

Memory 314 can store software modules that provide functionality when executed by processor 313. The modules can include, for example, an operating system 316 that can provide operating system functionality for the computer system 312, one or more inference engines 315A-315N configured to access and/or link to a plurality of segmentation models, such as those saved in the image segmentation model database 500, and an additional functionality module 317.

The inference engines 315A-315N are modules that include hardware and/or software components that are capable of executing algorithms according to the segmentation models stored in the image segmentation model database 500, such as, but not limited to, deep learning segmentation models, machine learning segmentation models, atlas based segmentation models, and shape or appearance based segmentation models.

The one or more inference engines 315A-315N can receive medical image data (whether training data or medical image(s) for inference) from image database 401, or image database 400 via network 600, or via I/O 319 and network 601 from medical imaging device 700 (i.e., planning medical images, for example), and/or images from radiotherapy system 100, and generate contours for one or more anatomical structures in the received medical images based on one or more of the image segmentation models stored in the image segmentation model database 500.

Figure 4:
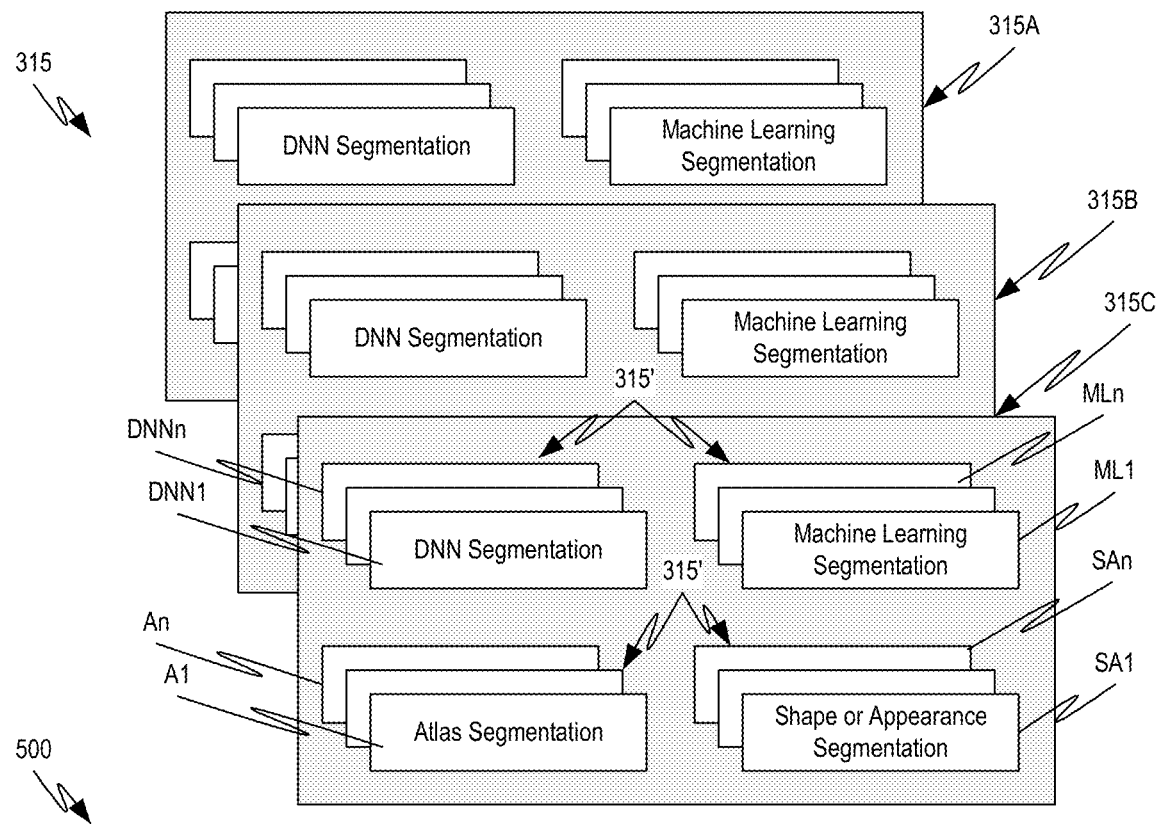
FIG. 4 is a simplified schematic diagram illustrating an exemplary inference engine set, according to various embodiments of the disclosed subject matter.

FIG. 4 shows an exemplary set of inference engines 315A-315C that can be used to generate contours of one or more anatomical structures. Each of the inference engines 315A-315C can include a plurality of inference modules 315', each including hardware/software components (DNN1-DNNn) capable of executing algorithms according to any suitable deep learning segmentation models, hardware/software components (ML1-MLn) capable of executing algorithms according to any suitable machine learning segmentation models, hardware/software components (A1-

An) capable of executing algorithms according to any suitable atlas based segmentation models, and hardware/software components (SA1-SAn) capable of executing algorithms according to any suitable shape or appearance based segmentation models, for example.

Alternatively, embodiments may include a single inference engine 315 that includes a plurality of inference modules 315' including hardware/software components capable of executing algorithms according to any suitable deep learning segmentation models, machine learning segmentation models, atlas based segmentation models, and shape or appearance based segmentation models.

Alternatively, embodiments may include a plurality of inference engines 315A-315N, each inference engine including an inference module 315' capable of executing algorithms according to a single type of segmentation model. For example, an exemplary embodiment may include inference engines 315A-315D, where inference engine 315A includes hardware/software components capable of executing algorithms according to deep learning segmentation models, inference engine 315B includes hardware/software components capable of executing algorithms according to machine learning segmentation models, inference engine 315C includes hardware/software components capable of executing algorithms according to atlas based segmentation models, and inference engine 315D includes hardware/software components capable of executing algorithms according to shape or appearance based segmentation models.

Alternatively, or additionally, embodiments may include a plurality of inference engines 315A-315N, with each inference engine including hardware/software components capable of executing algorithms of a single deep learning segmentation model. For example, a first inference engine 315A can include hardware/software components that can execute a first deep learning based segmentation model, a second inference engine 315B can include hardware/software components that can execute a second deep learning based segmentation model, and so on.

Alternatively, or additionally, embodiments may include a single inference engine including hardware/software components capable of executing algorithms of a single type of segmentation model.

In embodiments, the deep learning segmentation models stored in the image segmentation model database 500 can be based on any existing or later-developed neural network, or combinations thereof. Exemplary neural networks include, but are not limited to, a convolutional neural network (ConvNet or CNN) (e.g., U-Net, deep CNN, LeNet, V-Net, AlexNet, VGGNet, Xception, DenseNet, GoogLeNet/Inception, etc.), residual neural network (ResNet), recurrent neural network (RNN) (e.g., Hopfield, Echo state, independent RNN, etc.), long short-term memory (LSTM) neural network, recursive neural network, generative adversarial neural networks (GANs), and deep belief network (DBN).

In embodiments, the machine learning segmentation models stored in the image segmentation model database 500 can be based on any existing or later-developed supervised, unsupervised and reinforcement machine learning algorithms or any combinations thereof.

In embodiments, the atlas based segmentation models stored in the image segmentation model database 500 can be based on any existing or later-developed atlas based auto segmentation software, such as, but not limited to, Work-Flow Box (Mirada Medical), RTx (Mirada Medical), MultiPlan Autosegmentation (Accuray), iPlan (BrainLab), IMAgo (Dosisoft), MIM Maestro (MIM Software), SPICE (Philips), ABAS (Elekta), RayStation, ANACONDA (RaySearch Laboratories), Smart Segmentation (Varian), VelocityAI (Velocity), STAPLE, PLASTIMATCH, and/or any other atlas-based auto segmentation software.

In embodiments, the shape or appearance based model segmentation models stored in the image segmentation model database 500 can be based on any existing or later-developed shape or appearance based segmentation models, such as, but not limited to, principal component analysis (PCA) and Kernel PCA based models.

The inference engines 315A-315N can access the image segmentation database 500 via network 600 or can access a link to the image segmentation model database 500 via processor 313.

Figure 5:
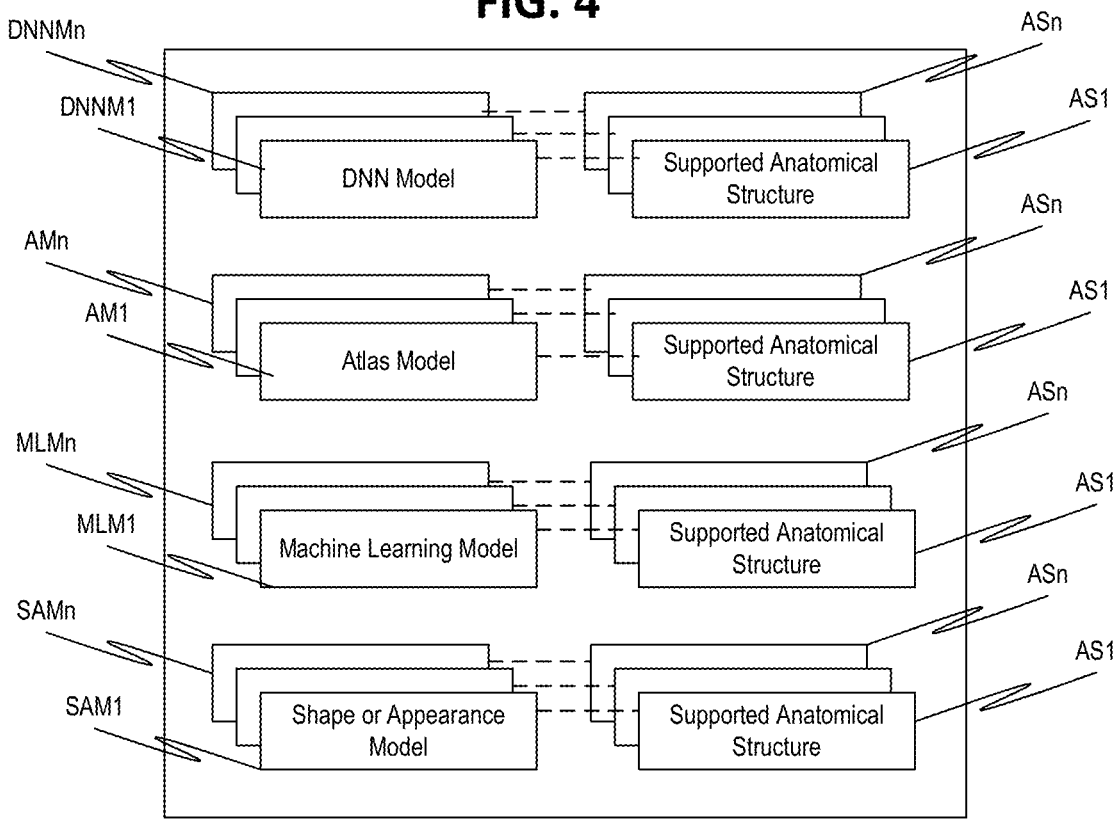
FIG. 5 is a simplified schematic diagram illustrating an exemplary image segmentation model database, according to various embodiments of the disclosed subject matter.

An exemplary image segmentation model database 500 is illustrated in FIG. 5. As shown in FIG. 5, the image segmentation model database 500 can include a library of segmentation models, including, but not limited to, a plurality of deep learning based segmentation models (DNNM1-DNNMn), a plurality of atlas based segmentation models (AM1-AMn), a plurality of machine learning based segmentation models (MLM1-MLMn), and a plurality of shape or appearance based segmentation models (SAM1-SAMn). Thus, each respective DNN model may run on a corresponding DNN engine contained in the inference engines 315A-315N, each respective atlas based model may run on a corresponding atlas based engine contained in the inference engines 315A-315N, each respective machine learning based model may run on a corresponding machine learning engine contained in the inference engines 315A-315N, and each shape or appearance based model may run on a corresponding shape or model based engine contained in the inference engines 315A-315N.

The image segmentation model database 500 can also include a list of anatomical structures (AS1-ASn) that each of the segmentation models in the database supports, corresponding model parameters, as well as additional information, including, but not limited to, the type of protocol that each of the anatomical structures (AS1-ASn) uses for contouring, and/or any relevant input data that each of the segmentation models in the library needs to perform the automatic segmentation task, such as, but not limited to, the types of images needed (i.e., CT, MRI, etc.) and/or possible guidance markers used or needed.

Although illustrated as containing a plurality of segmentation model types, alternatively, or additionally, the image segmentation model database 500 may include only deep learning based segmentation models, the corresponding supported anatomical structures, and corresponding relevant additional information.

In an exemplary embodiment, the segmentation model database 500 may include: (1) a convolutional neural network (CNN) based segmentation model supporting segmentation of the prostate (i.e., anatomical structure), in ultrasound images (i.e., imaging modality needed); (2) a deep belief network (DBN) based segmentation model supporting segmentation of the liver (i.e., anatomical structure) in CT images (i.e., imaging modality needed); (3) a convolutional neural network (CNN) based segmentation model supporting segmentation of the spinal cord (i.e., anatomical structure), in MRI images (i.e., imaging modality needed) using biomarkers (i.e., guidance markers); (4) a deep neural network (DNN) based segmentation model supporting segmentation of the prostate (i.e., anatomical structure), in CT images (i.e., imaging modality needed); (5) a deep neural network (DNN) based segmentation model supporting segmentation of the brain (i.e., anatomical structure), in MRI images (i.e., imaging modality needed); and (6) a fully convolutional neural network (FCNN) based segmentation model supporting segmentation of the head and neck (i.e., anatomical structures), in CT images (i.e., imaging modality needed).

The image segmentation model database 500 may further include additional deep learning based segmentation models and one or more of atlas based, machine learning based, and shape or appearance based automatic segmentation models, including, but not limited to: (7) shape representation model (SRM) for head and neck in CT images; (8) deformable shape model for prostate in ultrasound images; (9) hierarchical shape prior model for lungs, heart, and abdominal cavity in CT images; (10) atlas based segmentation model for prostate using CT images; (11) atlas based segmentation model for segmentation of the bladder, rectum and femoral heads in CT images, for example.

Alternatively, or additionally, the image segmentation model database 500 may include any combination of deep learning based segmentation models and any other current or future developed automatic segmentation models.

In embodiments, the image segmentation model database 500 is a previously generated database that one or more of the inference engines 315A-315N can access or can link to during deployment of the segmentation protocols.

In embodiments, the image segmentation models in the image segmentation model database 500 can be generated and/or trained prior to the deployment of segmentation protocols by the inference engines 315A-315N.

In embodiments, the image segmentation model database 500 can include a library of previously compiled trained automatic segmentation models that are accessible to different user/systems/frameworks/platforms, such as those described herein.

The image segmentation model database 500 may also include a library of parameters corresponding to each of the previously compiled trained automatic segmentation models.

In embodiments, the image segmentation model database 500 includes a library of previously compiled automatic segmentation models that are accessible to different user/systems/frameworks/platforms, such as those described herein, and which may be trained prior to being deployed by the inference engines 315A-315N. The image segmentation model database 500 may also include a library of parameters corresponding to each of the previously compiled automatic segmentation models.

The inference engines 315A-315N can access the segmentation models contained in the image segmentation model database 500 via network 600, or can access a link to the image segmentation model database 500 via processor 313. The processor 313 can retrieve any of the segmentation models stored in the image segmentation model database 500, as well as the list of anatomical structures (AS1-ASn) that each of the stored segmentation models supports, and parameters corresponding to each of the segmentation models, and any of the corresponding additional information stored in the image segmentation model database 500. Further, the processor 313 and the inference engines 315A-315N can operate to carry out the functions described below with respect to FIGS. 6-11.

Configurations and components for the image processing module, the networks, the medical imaging device, and the radiation therapy systems other than those specifically illustrated in FIG. 3 are also possible according to one or more contemplated embodiments.

Further, although the discussion of FIGS. 1-5 above has focused on the use of the image processing module 310 with a radiotherapy system 100, embodiments of the disclosed subject matter are not limited thereto. Indeed, the image processing module 310 may be provided as a separate independent system for image analysis, may be integrated with an imaging modality 700, may communicate with other medical treatment systems, or may be integrated with other medical treatment systems. Accordingly, embodiments of the disclosed image processing module 310 are not limited to the specific configuration illustrated in FIG. 1 or limited to use with radiotherapy systems, such as system 100.

Other variations and combinations will be readily apparent to one of ordinary skill in the art.

Figure 6:
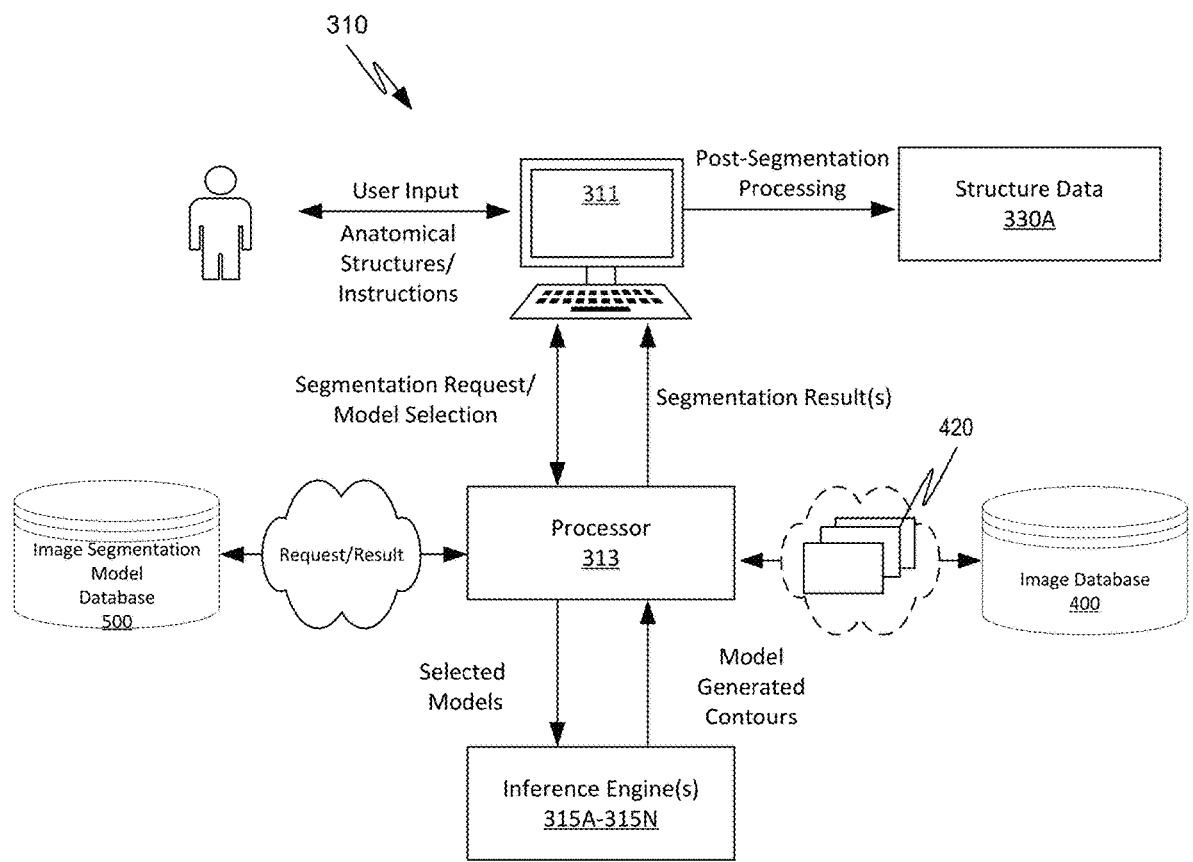
FIG. 6 is a simplified is schematic diagram illustrating an exemplary network-based multi-structure segmentation platform, according to various embodiments of the disclosed subject matter.

Referring to FIG. 6, an exemplary platform/framework and supported graphical user interface (GUI) tool is illustrated using the image processing module 310 to automatically generate a structure data 330A that includes contours of one or more anatomical structures on one or more medical images. The user 350 can input via the (GUI) 311, a list of the anatomical structures that the user desires to generate contours for, and corresponding input instructions for each of the desired anatomical structures. For example, the user 350 may desire to contour anatomical structure A (i.e., the target), anatomical structure B (i.e., an OAR), and anatomical structure C (i.e., the anatomy where both the target and the OAR are located). The user 350 can manually input anatomical structures A, B, C as the desired anatomical structures to be contoured via the (GUI) 311. Alternatively, the user 350 may also select via a drop-down menu displayed to the user 350 on the user interface 311, structures A, B, and C as the anatomical structures desired to be contoured. The user 350 may also input additional information and/or instructions relating to the patient's anatomy, shape, size and location of the patient's anatomy, target and OAR, as well as the type of medical image(s) that the contours are to be generated in.

Once the anatomical structures and related instructions are inputted by the user 350, a segmentation request can be sent via the I/O 319 to the processor 313 to generate a list of available segmentation models that support segmentation of at least one of the desired anatomical structures. Upon receiving the request, the processor 313 can access, via the network 600, the image segmentation model database 500, determine which ones of the segmentation models in the image segmentation model database 500 support segmentation of at least one of the desired anatomical structures, and generate a list of all available segmentation models in the database 500 that support at least one of the desired anatomical structures A, B, and C. The processor 313 can also generate a list of the anatomical structures (AS1-ASn) that each one of the available segmentation models supports.

The generated model list and supported anatomical structure list can be displayed to the user 350 for further selection. The user 350 can select from the displayed list of available segmentation models all or a subset of the segmentation models to be used to contour each one of the desired anatomical structures A, B, and C. For example, if the list included a first segmentation model supporting segmentation of anatomical structures A, B, C, and D, and a second segmentation model supporting segmentation of anatomical structures A and C, the user 350 may select the first segmentation model to be applied to contour: (1) A, B, and C; or (2) only A; or (3) only B; or (4) only C; or (5) A and B; or (6) A and C; or (7) B and C. The user 350 may also select the second segmentation model to be applied to contour: (1) A and C; or (2) only A; or (3) only C. The user 350 can also select only the first segmentation model to contour all of the desired anatomical structures A, B and C, and not select the second segmentation model at all.

The processor 313, upon receipt of the segmentation model selection for each one of the desired anatomical structures A, B, and C from the user 350, can access the image segmentation model database 500 via the network 600 to retrieve the selected segmentation models, and can provide the retrieved segmentation models to one or more inference engines 315A-315N for execution.

The processor 313 can supply the selected segmentation models to the inference engines 315A-315N in a consecutive fashion, namely, the processor 313 can retrieve the selected segmentation models from the segmentation model database 500 and send the selected models one by one to the inference engines 315A-315N for execution.

Alternatively, the processor 313 can supply the selected segmentation models to the inference engines 315A-315N simultaneously, namely, after retrieval of the selected segmentation models from the image segmentation model database 500, the processor 313 can send all of the selected models at the same time to one or more of the inference engines 315A-315N for execution.

The processor 313 can further send to the one or more inference engines 315A-315N, the list of the anatomical structures selected for contouring by each of the selected segmentation models. For example, if the user 350 selected the first segmentation model to contour A and B, and the second segmentation model to contour A and C, the processor 313 would send this information to the inference engines 315A-315N.

Alternatively, or additionally, the processor 313 may provide the one or more inference engines 315A-315N access to a link to the image segmentation model database 500, so that the inference engines can automatically deploy the selected segmentation models.

Upon receipt of the segmentation models and corresponding anatomical structures to be contoured, the inference engines 315A-315N can check whether the received/retrieved segmentation models do in fact support the anatomical structures on the list. For example, if the user 350 mistakenly selected the second segmentation model to contour anatomical structures B and C, the one or more inference engines 315A-315N would generate an error signal to indicate that the second segmentation model cannot support segmentation of anatomical structure B. If an error signal is generated, the user 350 can be prompted to review its selection of segmentation models and corresponding anatomical structures to be contoured, and allow the user 350 to select a proper combination of segmentation model and anatomical structure.

If the received/retrieved segmentation models do support the selected anatomical structures, the one or more inference engines 315A-315N can execute algorithms according to the received/retrieved segmentation models to generate corresponding contour data. The contour data includes contour data of all anatomical structures that each of the selected segmentation models support. For example, if the user 350 selected the first segmentation model for one or more of the desired anatomical structures A, B and C, the inference engines 315A-315N also generate contour data for anatomical structure D, since the first segmentation model also supports segmentation of anatomical structure D.

The processor 313 combines the generated contour data from inference engines 315A-315N with corresponding image data 420 retrieved from database 401 and/or database 400 via network 600 to obtain the contours of each of the anatomical structures supported by each of the selected segmentation models.

Since the inference engines 315A-315N may generate contours for anatomical structures not selected by the user 350 (i.e., anatomical structure D, for example), the processor 313 is further configured to automatically delete the contours for the anatomical structures not selected by the user 350 for contouring (i.e., contour for anatomical structure D, for example), prior to or after displaying the generated contours to the user 350 for further review and/or processing.

The processor 313 can also automatically modify the generated contours prior to or after displaying the generated contours to the user 350 for further review and/or processing. For example, the processor 313 can automatically modify the margins of the anatomical structures, and thus correspondingly modify the generated contours for the modified anatomical structures.

Figure 7A:
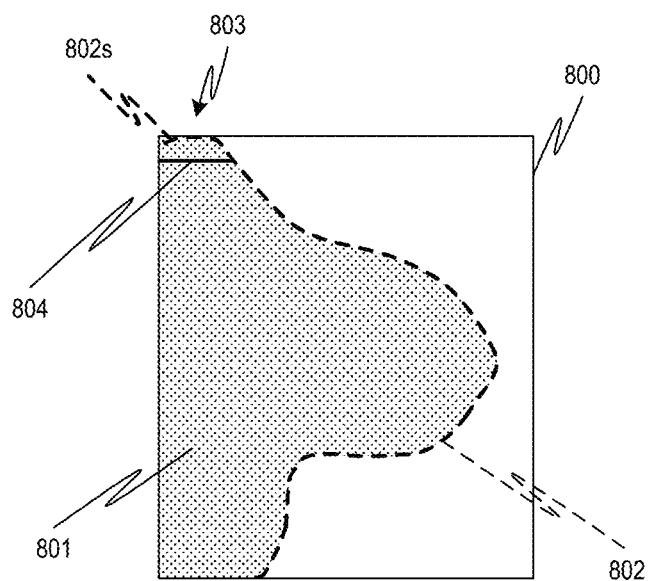
FIG. 7A is an illustration of a modified contour obtained for an anatomical structure, according to various embodiments of the disclosed subject matter.

FIG. 7A shows an exemplary automatic modification executed by processor 313 of a contour 802 generated for a breast 801. FIG. 7A shows a two-dimensional image 800 of a breast 801 with contour 802 generated by executing a selected segmentation model by one of the inference engines 315A-315N. Although the generated contour 802 includes a rounded contour 802s at the superior end 803 of the breast 801, the processor 313 can automatically modify the margin of the breast 801 using an axial cut 804 at the superior end of the breast 801. The contour 802 is thus automatically modified from a rounded contour at 802s to a cut contour at 804.

Figure 7B:
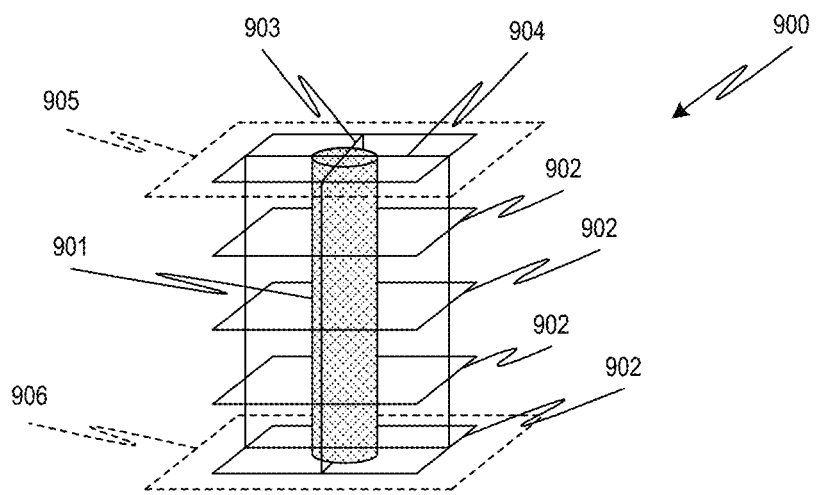
FIG. 7B is an illustration of an image stack containing contours of an anatomical structure, according to various embodiments of the disclosed subject matter.

The processor 313 can also automatically modify the generated contours by automatically rejecting specific contours. For example, FIG. 7B shows a stack 900 of computed tomography (CT) image slices containing the contour of an anatomical structure, such as a spine 901 for example, where 903 represent exemplary axial slices that are assembled to form a three-dimensional (3D) image. Each image slice 902 contains a portion of the contour generated for the anatomical structure 901. Corresponding 2D image slices in the sagittal direction 903 or coronal direction 904 can also be formed from the 3D image. In order to save time and processing resources, for example, the processor 313 may automatically reject one or more image slices 902, and thus reject the one or more contours contained in the rejected image slices 902. Specific rejected image slices may include image slices 905 and 906, for example, which are defining the top and bottom planes, and which may contain rounded contours for the spine.

The processor 313 is further configured to sends for display to the user 350, the contours that were generated for each of the desired anatomical structures A, B, and C by the inference engines 315A-315N. For example, if the first segmentation model was selected to generate contours for anatomical structures A and B, and the second segmentation model was selected to generate contours for anatomical structure B and C, the contours displayed to the user 350 are Contour A generated for anatomical structure A using the first segmentation model, Contour B1 generated for anatomical structure B using the first segmentation model, Contour B2 generated for anatomical structure B using the second segmentation model, and Contour C generated for anatomical structure C using the second segmentation model.

The user 350 may accept any of the generated contours or reject any of the generated contours. The user 350 may also combine the accepted contours. For example, for the two contours generated for the same anatomical structure B, the user 350 can either reject Contour B1 and accept Contour B2, or reject Contour B2 and reject Contour B1, or combine Contour B1 and Contour B2.

Optionally, the combining of the contours can be done using weighted values for each of the combined contours. For example, Contours B1 and B2 may be combined using a weighted value for each one, so as to obtain a Contour B that is a weighted combination of Contour B1 and Contour B2 (i.e., Contour B=$W_1$Contour B1+$W_2$Contour B2).

The contours may also be combined using Boolean operations, for example. Boolean operations include a set of logical rules by which contours can be combined. The four basic Boolean operations are AND, OR, Ex-OR (Exclusive OR) and NOT. Boolean operations can also be combined for more contour combinations. For example, given two contours for B, namely contour B1 and contour B2, the Boolean combination (B1 AND B2) generates a single contour B as a result. The contour B will contain only the pixels of the digital/binary images that are contained in both contours B1 and B2. A Boolean combination (B1 OR B2) generates a single contour B as a result, where contour B will contain the pixels in either contour B1 contour B2. A Boolean combination (B1 Ex-OR B2) also generates a single contour B as a result, containing the pixels which have a specific binary value (i.e., value "1" for example) in either image B1 or B2, but not if the pixels have that value in both contour B1 and B2. A Boolean combination (B1 NOT B2) requires only a single contour B1 or B2, and the result is a contour B where the pixels are reversed, namely, all pixels that had a particular value (i.e., value "1", for example) in the original contour will have a value "0" in the generated contour B, and the pixels that had a value "0" in the original contour will have a value "1" in the generated contour. A Boolean combination ((NOT B1) AND B2) will produce a contour B containing pixels that lie within contour B2 but outside contour B1. A Boolean combination (NOT (B1 AND B2)) generates a contour B containing pixels that do not have a value "1" in both B1 and B2. In a Boolean operation (B1-B2), the resulting contour B is a contour that contains contour B1 with the intersecting contour of B2 removed.

The contours may also be manually combined using a slider bar of the (GUI) 311, for example.

The user 350 may also reject any of the generated contours for any of the anatomical structures.

The user 350 may also be presented with the option of returning to the original list of available segmentation models generated by processor 313, and choose a different set of segmentation models to be executed by the inference engines 315A-315N to generate the contours for anatomical structures A, B and C.

The user 350 may also further process the generated contours for each of the desired anatomical structures A, B and C. For example, the user 350 can further modify the generated contours by manually or automatically cutting one or more of the generated contours at predefined locations.

In exemplary embodiments, the processor 313 can automatically locate the predefined locations upon user request.

In exemplary embodiments, the predefined locations include locations that contain rounded contours.

In exemplary embodiments, the predefined locations include locations where radiation is not expected.

In exemplary embodiments, the predefined locations are determined based on radiation field information.

Once post processing of the generated contours is finished by the user 350, the structure data 330A is generated. The structure data 330A includes the final contours of the desired anatomical structures in one or more originally specified medical images.

Figure 8:
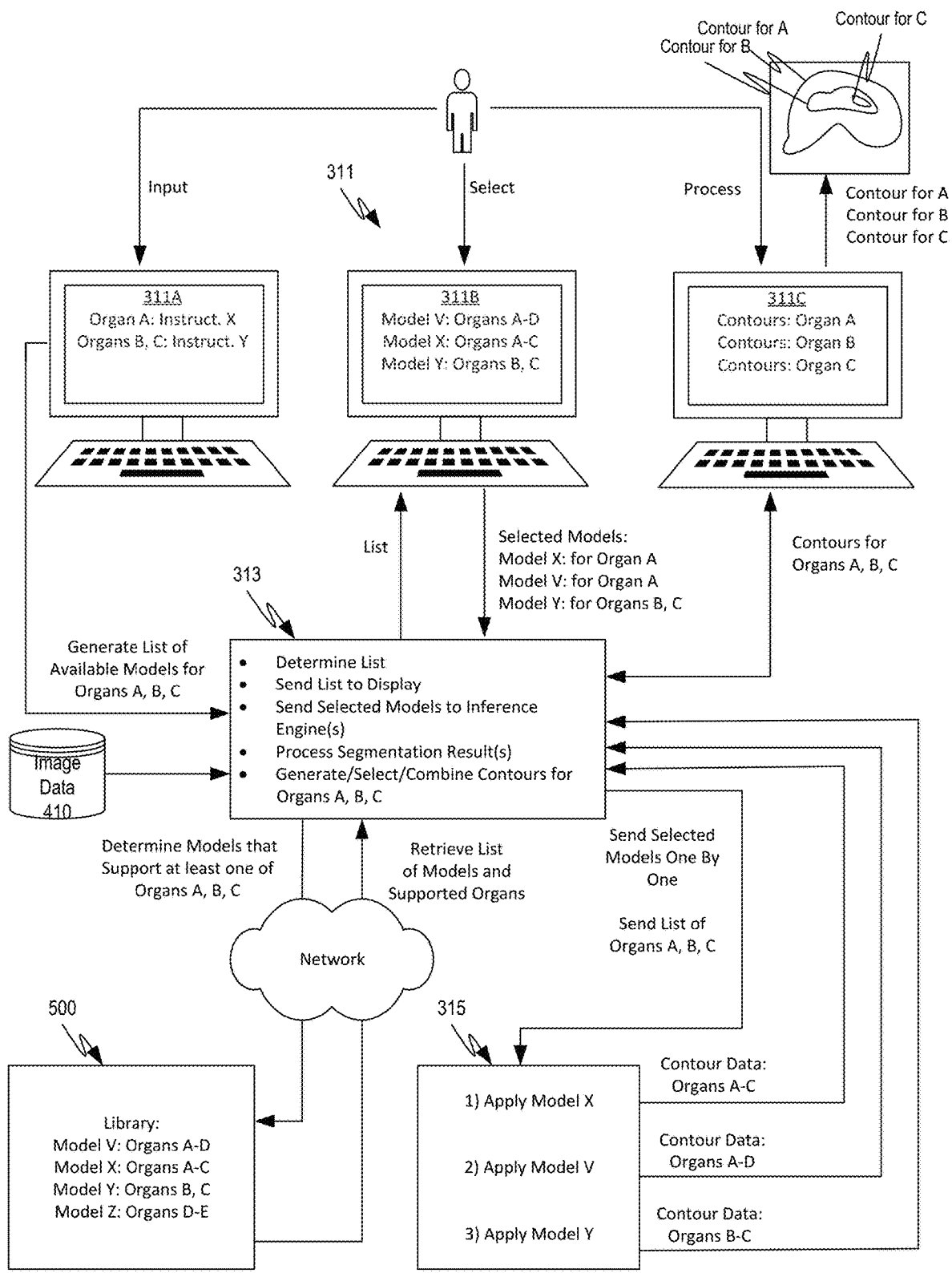
FIGS. 8-9 are simplified schematic diagrams illustrating different aspects of multi-structure segmentation processes using different segmentation models, according to various embodiments of the disclosed subject matter.

FIG. 8 illustrates another exemplary platform/framework and supported graphical user interface (GUI) tool to automatically generate a structure data including contours of one or more anatomical structures on one or more images.

The user 350 can input via the (GUI) 311, a list of the anatomical structures that the user desires to generate contours for, and corresponding input instructions for each of the desired anatomical structures. For example, the user 350 may desire to contour organ A, organ B, and organ C. The user 350 can manually input the name of the organs A, B, C as the desired anatomical structures to be contoured at an input display 311A of the (GUI) 311. The user 350 may also select via a drop-down menu displayed to the user 350 at the user interface 311, organs A, B, and C as the anatomical structures desired to be contoured. The user 350 may also input additional information and/or instructions relating to the patient's anatomy, shape, size and location of the patient's anatomy, target and OAR, image type, etc., at the input display 311A.

Once the organ names and related instructions are inputted by the user 350, a segmentation request can be sent via the I/O 319 to the processor 313 to generate a list of available segmentation models that support segmentation of at least one of organs A, B, and C. Upon receiving the request, the processor 313 accesses, via the network 600, the image segmentation model database 500, and determines which ones of the segmentation models in the database 500 support segmentation of at least one of organs A, B and C. The processor 313 then generates a list of all available segmentation models that support at least one of organs A, B, and C. The processor 313 also generates a list of the anatomical structures that each one of the available segmentation models supports. In an exemplary embodiment, the list of segmentation models and supported anatomical structures includes Model V: Organs A-D; Model X: Organs A-C; Model Y: Organs B-C.

The generated lists can be displayed to the user 350 for further selection. The user 350 can select, at a selection display 311B of the GUI 311, from the displayed list of available segmentation models all or a subset of the segmentation models to be used to contour each one of the desired anatomical structures A, B, and C. In an exemplary embodiment, the user 350 selected Model X for Organ A; Model V for Organ A, and Model Y for Organs B and C.

The processor 313 receives the model selection from the user 350, accesses the image segmentation model database 500 via the network 600 to retrieve the selected segmentation models (i.e., Model V, Model X, Model Y), and provides the retrieved segmentation models one by one to inference engine 315 for execution.

The processor 313 also sends the list of the anatomical structures selected for contouring by each of the selected segmentation models, namely, Model X for A, Model V for A, and Model Y for B and C.

Alternatively, the processor 313 may provide the inference engine 315 access to a link to the segmentation model database 500, so that the inference engine can automatically deploy the selected segmentation models.

The inference engine executes algorithms according to the received segmentation models to generate corresponding contour data. Since it received the segmentation model X first, the inference engine 315 executes segmentation model X first and generates contour data for organs A, B, and C, then segmentation model V to generate contour data for organs A, B, C, and D, followed by the execution of segmentation model Y to generate contour data for organs B and C.

The processor 313 can combine the generated contour data from the inference engine 315 with corresponding image data retrieved from image database 401 and/or image database 400 via network 600 to obtain the contours for organs A, B, C, and D.

Since organ D was not selected by the user 350 as one of the desired anatomical structures, the processor 313 can automatically delete the contour generated for organ D.

The processor 313 can also automatically modify the contours generated for organs A, B, and C prior to displaying it to the user 350. For example, the processor 313 can automatically modify the margins of any of the organs A, B and C on the image, and correspondingly modify the generated contours for the modified organs.

The processor 313 can also automatically modify the generated contours by automatically rejecting specific contours. For example, if processor 313 determines that organ C is not an organ that is likely to be irradiated with radiation, processor 313 can automatically reject contour C.

The processor 313 then sends to the user 350 for display at a processing display 311C of GUI 311, the contours that were generated for each of the selected organs A, B, and C by the selected segmentation models, namely, a first contour for organ A generated by segmentation model X, a second contour for organ A generated by segmentation model V, a contour for organ B generated by segmentation model Y and a contour for C generated by segmentation model Y.

The user 350 may accept any of the generated contours or reject any of the generated contours. The user 350 may also combine the accepted contours. For example, for the two contours generated for the same organ A, the user 350 can either reject or accept one or both of the generated contours. If both contours for organ A are accepted, the user 350 may combine the two contours using different combining methods. For example, the two contours generated for organ A can be combined using Boolean operators. The two contours for organ A can also be combined on a weighted value basis (contour A=$w_1$contour $A_1$+$w_2$contour $A_2$). The two contours for organ A can also be manually combined by the user 350 using the slider of the GUI 311.

Although specific combination methods have been described, it is to be understood that the contours can be combined using any other applicable combination methods.

The user 350 may also reject any of the generated contours, and choose to return to the selection display 311B of the GUI 311 and select different segmentation models from the displayed list to generate the contours for organs A, B and C. Once the user 350 selects one or more different segmentation models from the list, the generation of the contours follows the same steps as with the original model selection.

The accepted final contours for organs A, B and C will be contained in the structure data 330A, to be optionally further processed for dose data 330B.

Figure 9:
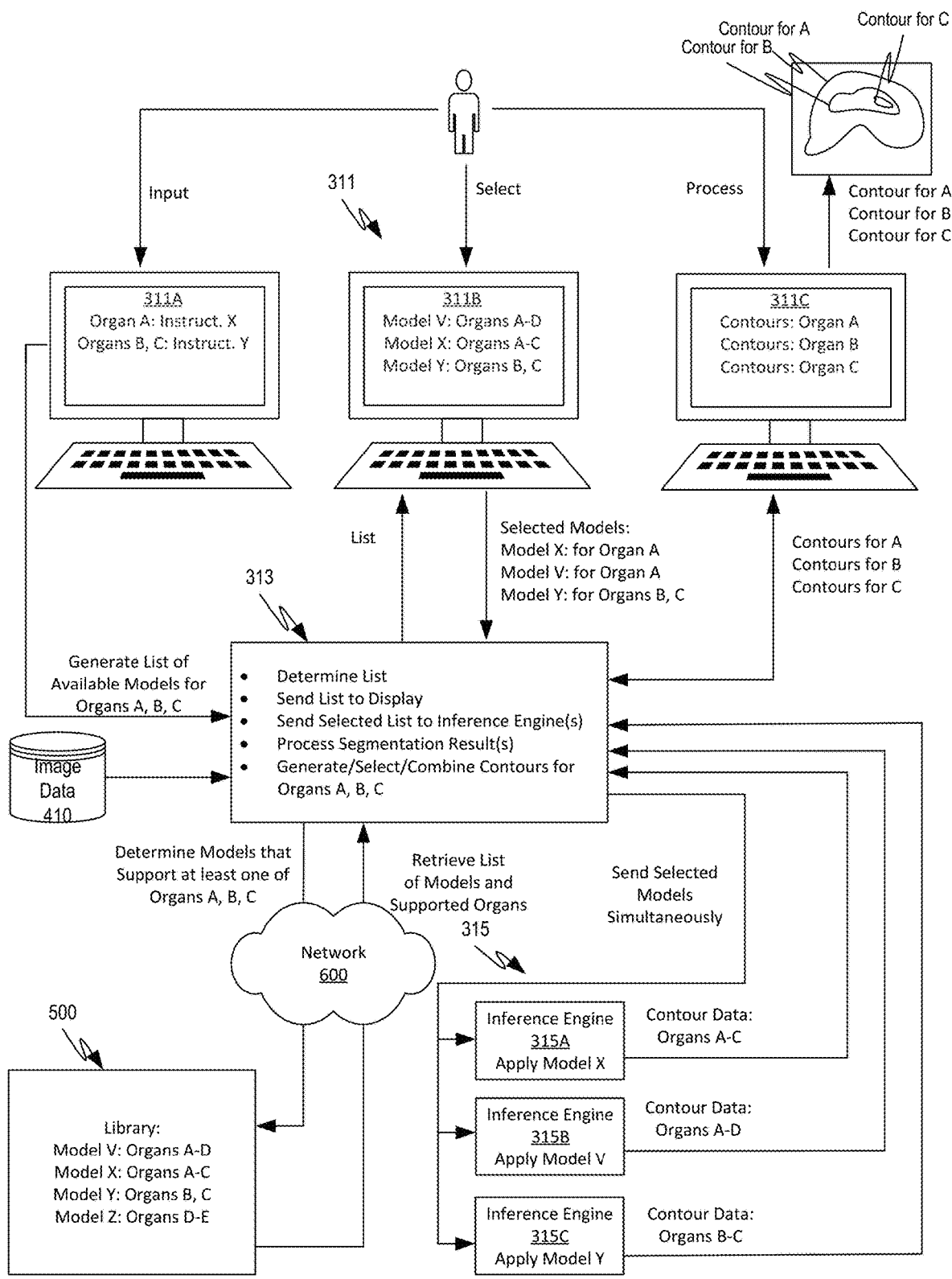

FIG. 9 illustrates another exemplary platform/framework and supported graphical user interface (GUI) tool to automatically generate a structure data including contours of one or more anatomical structures on one or more images. This platform/framework is similar to the one presented in FIG. 8, the difference being that, instead of using a single inference engine 315 that consecutively receives the segmentation models selected to be used to segment each of the desired organs A, B, C, a plurality of inference engines 315A-315C are used so as to be able to simultaneously receive and apply the different segmentation models.

As in the previous platform/framework, the user 350 can input via the (GUI) 311, a list of the anatomical structures that the user desires to generate contours for, and corresponding input instructions for each of the desired anatomical structures. For example, the user 350 may desire to contour organ A, organ B, and organ C. The user 350 can manually input the name of the organs A, B, C as the desired anatomical structures to be contoured at an input display 311A of the (GUI) 311. The user 350 may also select via a drop-down menu displayed to the user 350 at the user interface 311, organs A, B, and C as the anatomical structures desired to be contoured. The user 350 may also input additional information and/or instructions relating to the patient's anatomy, shape, size and location of the patient's anatomy, target and OAR, image type, etc., at the input display 311A.

Once the organ names and related instructions are inputted by the user 350, a segmentation request can be sent via the I/O 319 to the processor 313 to generate a list of available segmentation models that support segmentation of at least one of organs A, B, and C. Upon receiving the request, the processor 313 accesses, via the network 600, the image segmentation model database 500, determines which ones of the segmentation models in the database 500 support segmentation of at least one of organs A, B and C. The processor 313 then generates a list of all available segmentation models that support at least one of organs A, B, and C. The processor 313 also generates a list of the anatomical structures that each one of the available segmentation models supports. In an exemplary embodiment, the list of segmentation models and supported anatomical structures includes Model V: Organs A-D; Model X: Organs A-C; Model Y: Organs B-C.

The generated lists can be displayed to the user 350 for further selection. The user 350 can select, at a selection display 311B of the GUI 311, from the displayed list of available segmentation models all or a subset of the segmentation models to be used to contour each one of the desired anatomical structures A, B, and C. In an exemplary embodiment, the user 350 selected Model X for Organ A; Model V for Organ A, and Model Y for Organs B and C.

The processor 313 receives the model selection from the user 350, accesses the image segmentation model database 500 via the network 600 to retrieve the selected segmentation models (i.e., Model V, Model X, Model Y), and provides the retrieved segmentation models simultaneously to inference engines 315A-315C for execution. For example, segmentation model X can be sent to inference engine 315A, segmentation model V can be sent to inference engine 315B, and segmentation model Y can be sent to inference engine 315C.

The processor 313 also sends the list of the anatomical structures selected for contouring by each of the selected segmentation models, namely, Model X for A, Model V for A, and Model Y for B and C.

Alternatively, the processor 313 may provide the inference engines 315A-315C access to a link to the image segmentation model database 500, so that the inference engine can automatically deploy the selected segmentation models.

Each of the inference engines 315A-315C execute suitable algorithms according to the received segmentation models to generate corresponding contour data.

The processor 313 can combine the generated contour data from the inference engine 315 with corresponding image data retrieved from image database 401 and/or image database 400 via network 600 to obtain the contours for organs A, B, C, and D. Since organ D was not selected by the user 350 as one of the desired anatomical structures, the processor 313 can automatically delete the contour generated for organ D.

The processor 313 can also automatically modify the contours generated for organs A, B, and C prior to displaying it to the user 350. For example, the processor 313 can automatically modify the margins of any of the organs A, B and C on the image, and correspondingly modify the generated contours for the modified organs.

The processor 313 can also automatically modify the generated contours by automatically rejecting specific contours. For example, if processor 313 determines that organ C is not an organ that is likely to be irradiated with radiation, processor 313 can automatically reject contour C.

The processor 313 then sends to the user 350 for display at a processing display 311C of GUI 311, the contours that were generated for each of the selected organs A, B, and C by the selected segmentation models, namely, a first contour for organ A generated by segmentation model X, a second contour for organ A generated by segmentation model V, a contour for organ B generated by segmentation model Y and a contour for C generated by segmentation model Y.

The user 350 may accept any of the generated contours or reject any of the generated contours. The user 350 may also combine the accepted contours. For example, for the two contours generated for the same organ A, the user 350 can either reject or accept one or both of the generated contours. If both contours for organ A are accepted, the user 350 may combine the two contours using different combining methods. For example, the two contours generated for organ A can be combined using Boolean operators. The two contours for organ A can also be combined on a weighted value basis (contour A=$w_1$contour $A_1$+$w_2$contour $A_2$). The two contours for organ A can also be manually combined by the user 350 using the slider of the GUI 311.

Although specific combination methods have been described, it is to be understood that the contours can be combined using any other applicable combination methods.

The user 350 may also reject any of the generated contours, and choose to return to the selection display 311B of the GUI 311 and select different segmentation models from the displayed list to generate the contours for organs A, B and C. Once the user 350 selects one or more different segmentation models from the list, the generation of the contours follows the same steps as with the original model selection.

The accepted final contours for organs A, B and C will be contained in the structure data 330A, to be optionally further processed for dose data 330B.

Figure 10:
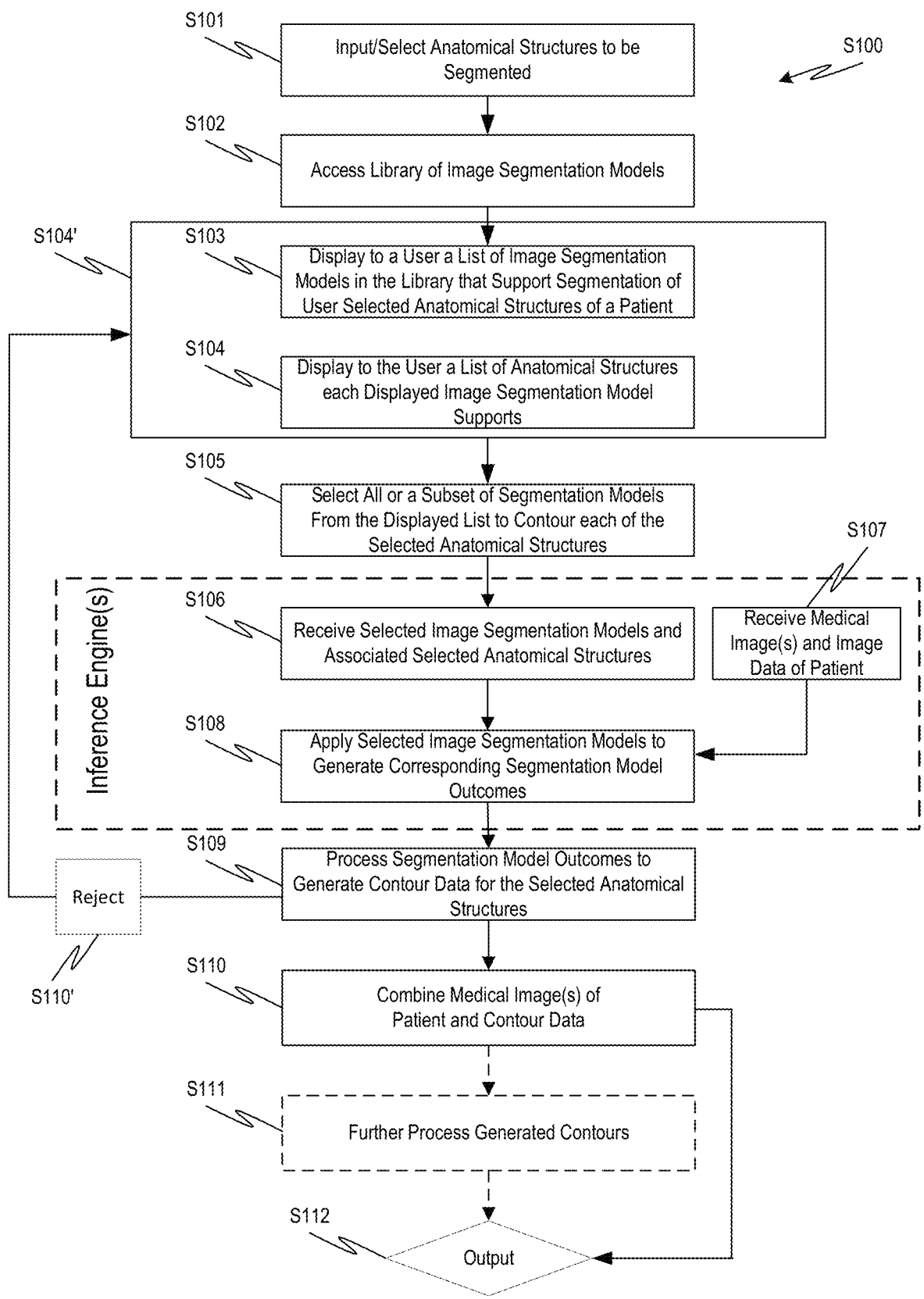
FIGS. 10-13 are different process flows for multi-structure segmentation using different segmentation models, according to various embodiments of the disclosed subject matter.

FIGS. 10-13 schematically illustrate exemplary network-based automatic segmentation processes for multiple organs using multiple segmentation models. FIG. 10 illustrates an automatic multi-organ multi segmentation model segmentation process S100.

In step S101, a user inputs the anatomical structures of a patient it desires to contour or selects the anatomical structures from an automatically generated list displayed on a display screen. The anatomical structures may include one or more or a combination of, targets (i.e., tumor), organs, organs at risk, tissues, blood vessels, bones, etc.

In step S102, a database containing a library of different automatic segmentation models is accessed. In step S103, a list of all available segmentation models in the library which support segmentation of at least one of the selected anatomical structures is displayed to the user. A list of all anatomical structures that each of the displayed segmentation models supports is also displayed to the user in step S104. The display steps S103 and S104 together are indicated as step S104'. Any other additional information regarding the segmentation models and supported anatomical structures can also be displayed to the user.

In step S105, the user selects all or a subset of the displayed segmentation models for use for each of the selected anatomical structures desired to be contoured. One or more inference engines 315A-315N receive the selected segmentation models and the list of associated selected anatomical structures in step S106, and apply in step S108, the selected segmentation models to generate corresponding segmentation outcomes (i.e., contour data) on one or more image data of the patient received in step S107. In step S109, the generated segmentation outcomes are processed to generate contour data for the selected anatomical structures. In step S110, the contour data generated in step S109 is combined with one or more medical images of the patient to obtain the contours of the selected anatomical structures as structure data output in step S112.

Optionally, the segmentation outcomes can be rejected in step S110' prompting the process S100 to return to step S104', so as to allow the user to select in S105 a different set of segmentation models to be applied in steps S106-S108 to generate different segmentation outcomes.

Optionally, the contour data on medical images obtained in step S110 can be further processed in step S111.

Figure 11:
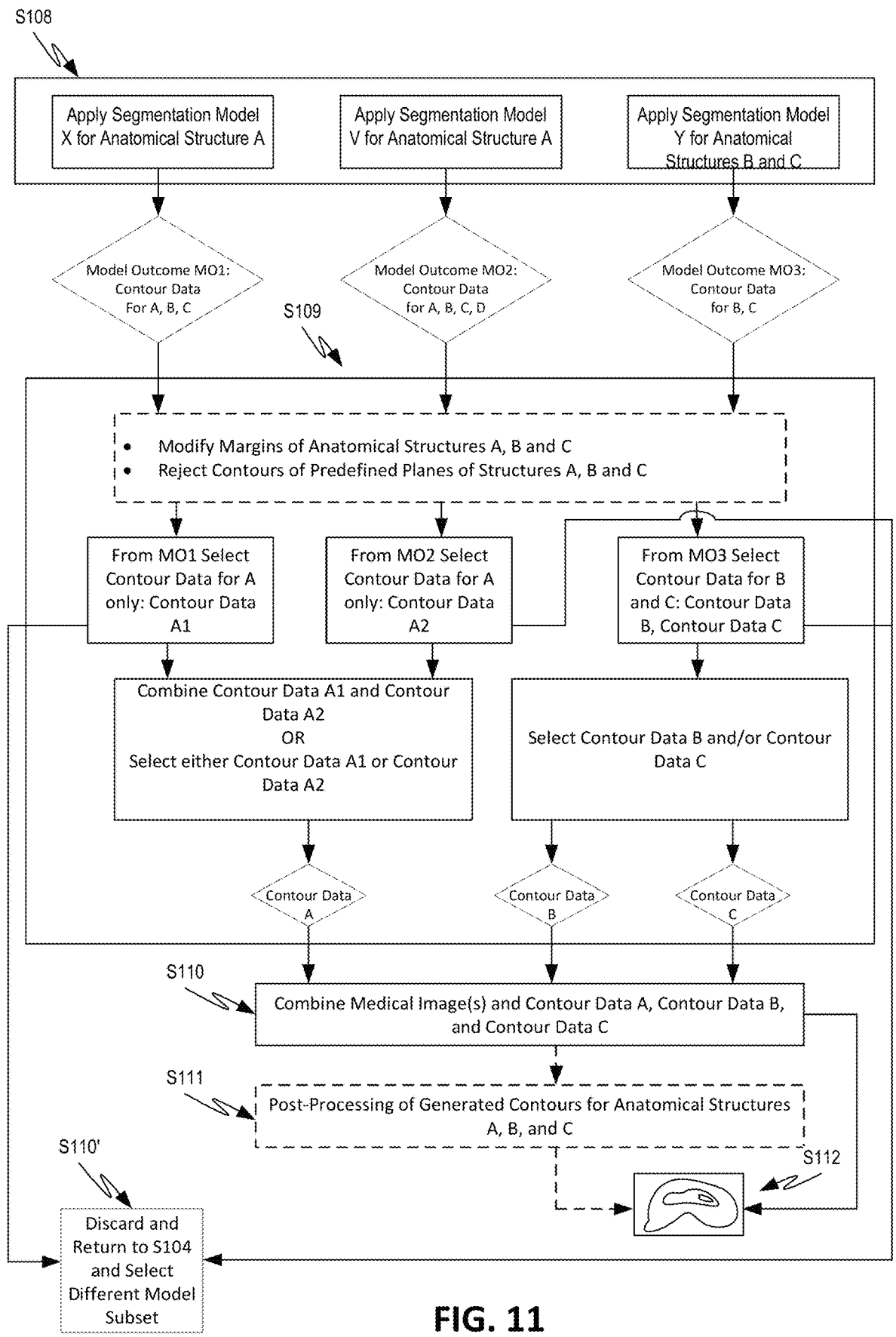

FIG. 11 illustrates exemplary automatic segmentation process steps S108-S112 of a process S100, in which the user selected anatomical structures A, B, and C to be segmented in step S101, the available segmentation models in the segmentation model library supporting at least one of the selected anatomical structures A, B, and C were models X, Y, Z, V and Q, with model X supporting segmentation of anatomical structures A, B and C, model Y supporting segmentation of anatomical structures B and C, model Z supporting segmentation of anatomical structures A and D, model V supporting segmentation of anatomical structures A, B, C and D, and model Q supporting segmentation of anatomical structure C, for example (steps S102-S104'), and where the user selected in step S105, model X and model V to segment structure A, and model Y to segment structures B and C.

As shown in FIG. 11, one or more of the inference engines 315A-315N receive the selected segmentation models X, V, and Y and selected corresponding anatomical structures, and apply the algorithms suitable for each of the received segmentation models, to generate corresponding segmentation model outcomes (MOs). In the exemplary embodiment of FIG. 11, by applying the selected segmentation models X, V, and Y, a first segmentation model outcome MO1, a second segmentation model outcome MO2, and a third segmentation model outcome MO3 is generated, one for each respective segmentation model applied. Since model X supports segmentation of structures A, B and C, segmentation model outcome MO1 includes contour data for structures A, B and C. Since model V supports segmentation of structures A, B, C and D, segmentation model outcome MO2 includes contour data for structures A, B, C, and D. Since segmentation model Y supports segmentation of structures B and C, the segmentation model outcome MO3 includes contour data for structures B and C.

The processing of the segmentation model outcomes MO1, MO2, and MO3 in step S109 can exemplarily include selection of contour data only for the selected anatomical structures A, B and C, for example. This can include selection of contour data for anatomical structure A from segmentation model outcome MO1 (i.e., A1), the selection of contour data for anatomical structure A from segmentation model outcome MO2 (i.e., A2), and the selection of contour data for anatomical structures B and C from segmentation model outcome MO3.

Processing step S109 can further include steps for selecting, and/or combining, and/or rejecting the contour data obtained for each of the selected anatomical structures from the plurality of segmentation model outcomes.

For example, contour data A1 may be combined with contour data A2 to generate a combined contour data A for anatomical structure A. Alternatively, contour data A1 may be rejected and contour data A2 may be accepted as the contour data A for anatomical structure A. Alternatively, contour data A2 may be rejected and contour data A1 may be selected as the contour data for anatomical structure A. Alternatively, both contour data A1 and contour data A2 may be rejected.

Contour data B and C obtained for anatomical structures B and C can also be accepted or rejected by the user. For any and all rejected contour data, the user is provided with the option in step S110' to return to the display screen of step S104' and again select in step S105 a different set of segmentation models to be applied to contour the selected anatomical structures A, B and C.

Optionally, step S109 may also include steps for automatically processing the segmentation model outcomes from step S108. For example, the margins of any or all of the selected anatomical structures A, B and C may be modified, so that the contour data generated for that particular anatomical structure is also automatically modified.

Another optional processing step includes automatically rejecting certain segmentation model outcomes. This could include automatically rejecting the contour data for B and C from segmentation model outcome MO1, and automatically rejecting contour data for B, C and D from segmentation model outcome MO2, for example. Another optional step could include automatically rejecting contour data obtained for certain image planes for the selected structures A, B and C, from the segmentation model outcomes MO1-MO3. For example, if contour data for A from MO1 includes contour data in five different image planes, but only two of those planes are determined to be useful, the contour data for the three additional planes could be automatically be discarded, for example.

The contour data for each of the selected anatomical structures A, B, and C obtained in S109 can be combined with one or more medical images for the patient in S110, so as to be displayed as the final contours for the anatomical structures A, B and C of structure data 330A in step S112.

Optionally, the contours obtained in S110 can be further processed in steps S111. For example, the user may decide to manually modify via the user interface GUI 311 the generated contours. Additionally, or alternatively, the user may modify any one of the generated contours by cutting any one of the generated contours, so that the contours along the cut are straight instead of rounded. The cutting may be done manually or automatically. When done automatically, the user may prompt the processor 313 to locate locations along which modify the one or more contours and modify the contours so as to include a straight edges along the cut instead of the generated round edges.

Figure 12:
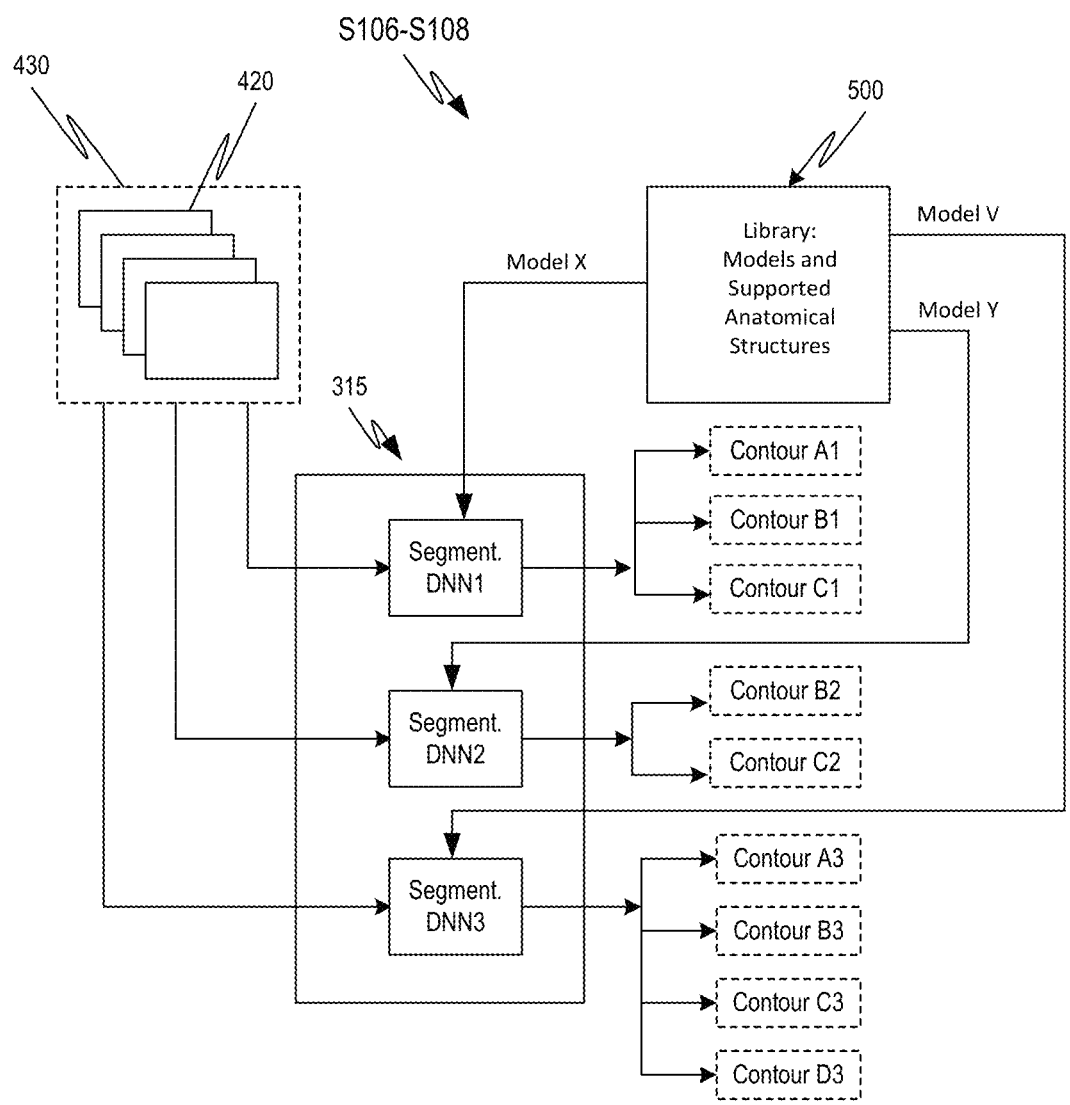
Figure 13:
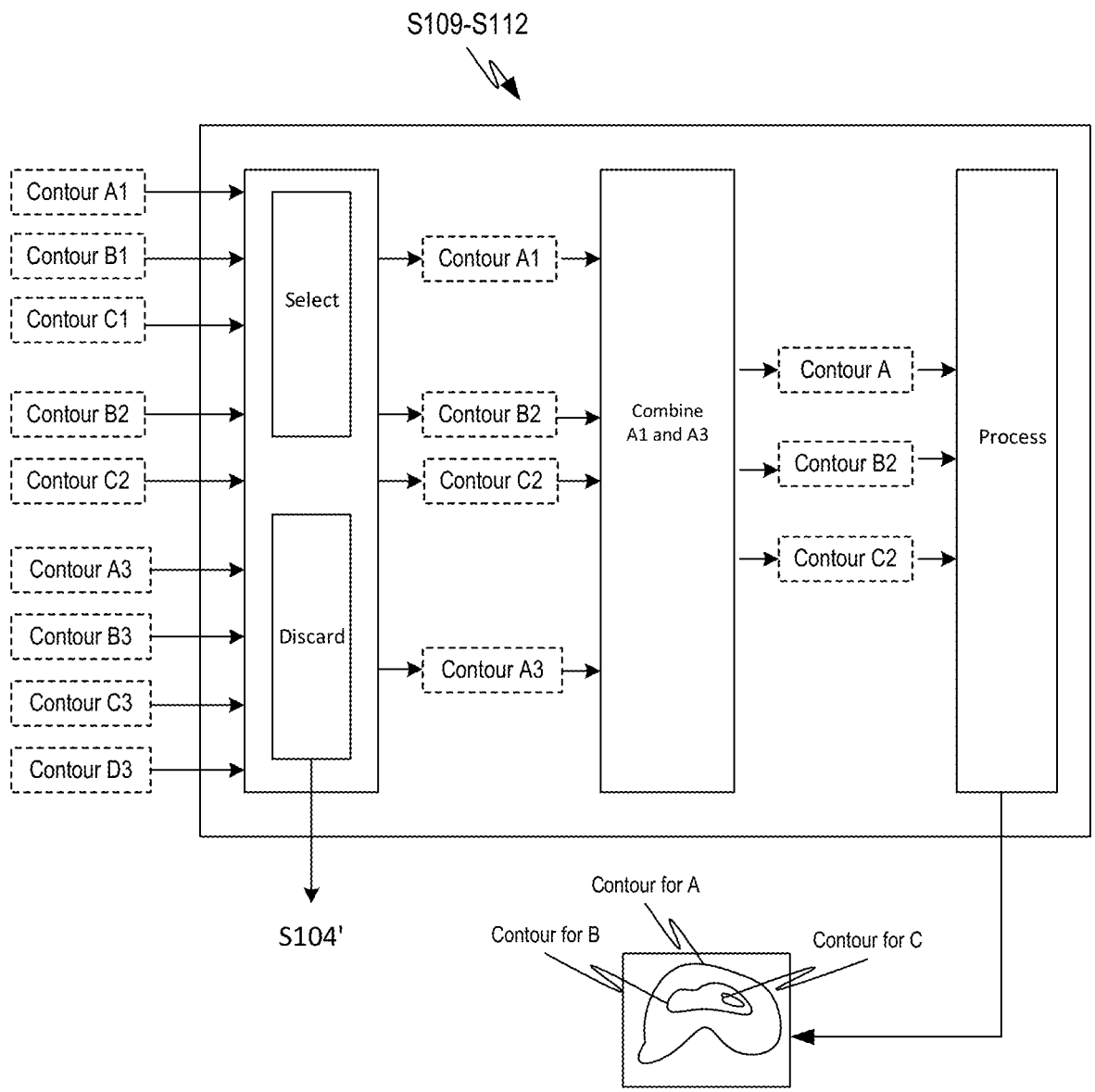

FIGS. 12-13 illustrate exemplary automatic segmentation process steps S106-S112 of a process S100, in which the user selected anatomical structures A, B, and C to be segmented in step S101, the available segmentation models in the segmentation model database 500 supporting at least one of the selected anatomical structures A, B, and C were models X, Y, Z, V and Q, with model X being a DNN segmentation model supporting segmentation of anatomical structures A, B and C, model Y being a DNN segmentation model supporting segmentation of anatomical structures B and C, model Z being an atlas based segmentation model supporting segmentation of anatomical structures A and D, model V being a DNN segmentation model supporting segmentation of anatomical structures A, B, C and D, and model Q being a shape segmentation model supporting segmentation of anatomical structure C, for example (steps S102-S104'), and where the user selected in step S105 model X and model V to segment structure A, and model Y to segment structures B and C, for example.

In step S108, three different inference modules (DNN1-DNN3) of a single inference engine 315 (or three different inference engines 315A-315C, with 315A supporting DNN1, 315B supporting DNN2, and 315C supporting DNN3, for example) receive the selected models X, Y, and V, simultaneously or consecutively, and by applying suitable DNN segmentation algorithms supported by corresponding DNN engines (DNN1-DNN3), generate corresponding DNN segmentation outcomes, such as contour A1, contour B1 and contour C1 from DNN1, contour B2 and contour C2 from DNN2, and contours A3, B3, C3 and D3 from DNN3 based on image of one (430) or a plurality of image slices (430) received in step S107.

The contours obtained in step S108 can be processed in steps S109-S112 by applying one or more selecting/combining/accepting/rejecting/discarding steps to, for example, select contours A1, B2, C2, and A3, combining contours A1 and A3 to obtain contour A, discarding contours B1, C1, B3, C3 and D3, and displaying contours A, B2 and C2 on one or more images as outcome of step S112. It is to be understood that the selecting/combining/accepting/rejecting/discarding methods disclosed throughout this disclosure can be applied. It is also to be understood that any other suitable selecting/combining/accepting/rejecting/discarding methods may also be applied.

Optionally, contours A, B1 and C1 could be further processed in S109, and/or discarded, and process S100 returned to step S104' for selection of different set of segmentation models. It is to be understood that any of the optional/selective processing options described throughout this disclosure may be applied. It is also to be understood that any other suitable processing methods may be applied.

Figure 14:
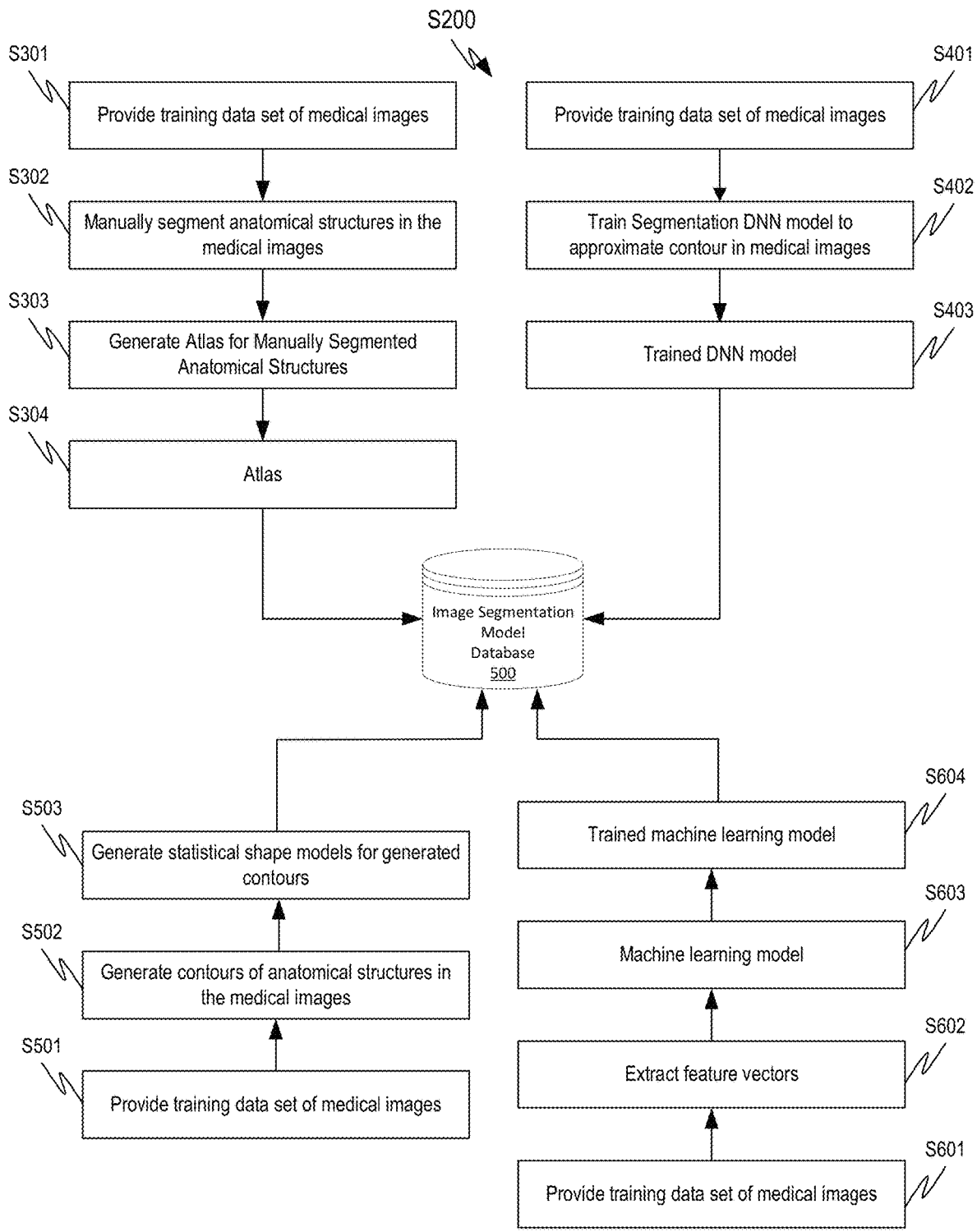
FIG. 14 is a simplified process flow for generating a library of different automatic segmentation models, according to various embodiments of the disclosed subject matter.

FIG. 14 illustrates an exemplary method S200 by which the library of different segmentation models in the image segmentation model database 500 can be generated. For example, in order to generate a plurality of atlas based automatic segmentation models, a plurality of anatomical structures can be manually contoured in one or more medical images obtained in S301 from image database 400 or image database 401. For each of the generated contours, an atlas is then generated in S303, by any suitable currently available or future developed atlas generating protocols, and the plurality of so obtained atlases can be stored in the image segmentation model database 500.

To generate trained DNN segmentation models for the database 500, in step S402, a DNN model obtains a training data sets of medical images from the image database 400 or 401 in step S401. The training data set can include 2-D or 3-D images with ground truth contours for the anatomical structures imaged by the different pixels or voxels. The training data set can include additional ground truth information, such as cut-off plane location and/or user-defined regions of interest, or any other ground truths.

As previously discussed, a DNN model refers to a class of computer-based machine-learning algorithms that utilize many layers or stages (in particular, at least two "hidden" layers between input and output layers) of data processing for feature learning, pattern analysis, and/or classification. In general, these DNN models are formed by a layered network of processing elements (referred to as neurons or nodes) that are interconnected by connections (referred to as synapses or weights). The layers of nodes are trained from end-to-end (i.e., from input layer to output layer) to extract feature(s) from the input and classify the feature(s) to produce an output (e.g., classification label or class). Open-source frameworks, such as Tensorflow or PyTorch, for example, can be used to generate such DNN models.

In step S402, the DNN model is trained to approximate contours of one or more anatomical structures in the medical images obtained in step S401. Training involves determining one or more parameters of nodes in hidden layers of the DNN model, for example, by an iterative process that varies parameters such that the DNN model output more closely matches corresponding ground truth. The trained DNN models obtained in S403 are then stored in the image segmentation model database 500.

Figure 15:
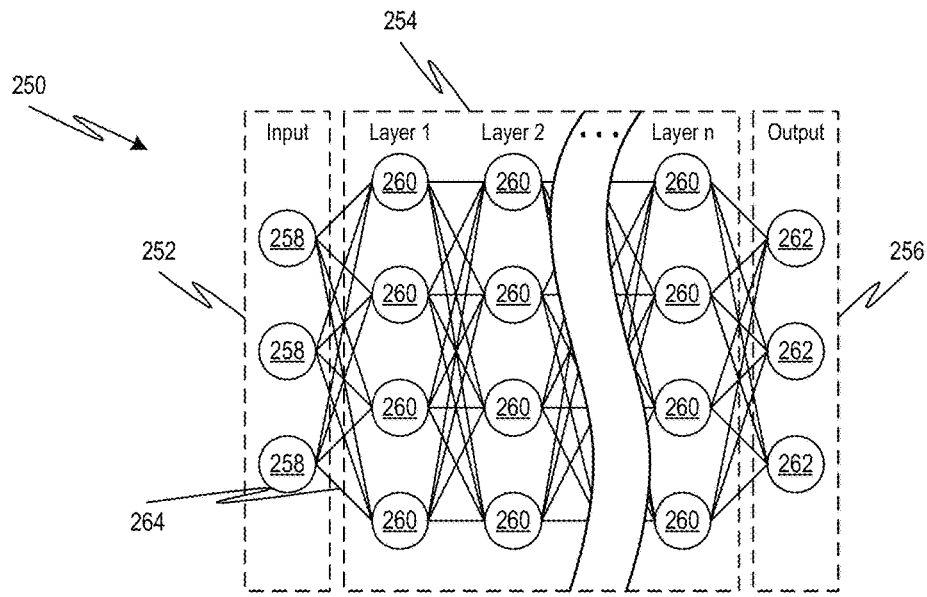
FIG. 15 a simplified process flow for generating a library of different automatic DNN segmentation models, according to various embodiments of the disclosed subject matter.

FIG. 15 illustrates a simplified node map 250 for an exemplary DNN model. The DNN model includes a stack of distinct layers (vertically oriented in FIG. 15) that transform an input (provided to the nodes 258 of input layer 252) into an output (at nodes 262 of output layer 256). The intervening layers (Layer 1 through Layer n) between the input layer 252 and output layer 256 are referred to as "hidden" layers 254. At least two hidden layers are provided in order for the neural network to be considered "deep." Each hidden layer has respective nodes 260, which perform a particular computation and are interconnected to nodes in adjacent layers. For example, each node 260 can include a weighting function, which provides weights to respective inputs, and an activation function, which processes the weighted inputs to generate respective outputs. The different hidden layers 254 can include, but are not limited to, final loss layers, non-linear operator layers, pooling layers, subsampling layers, fully connected layers, and convolutional layers. Although FIG. 15 illustrates the hidden layers 254 as having more nodes 260 per layer than a number of the nodes 258/262 in the input 252 and output 256 layers, other numbers and configurations are also possible.

Figure 16:
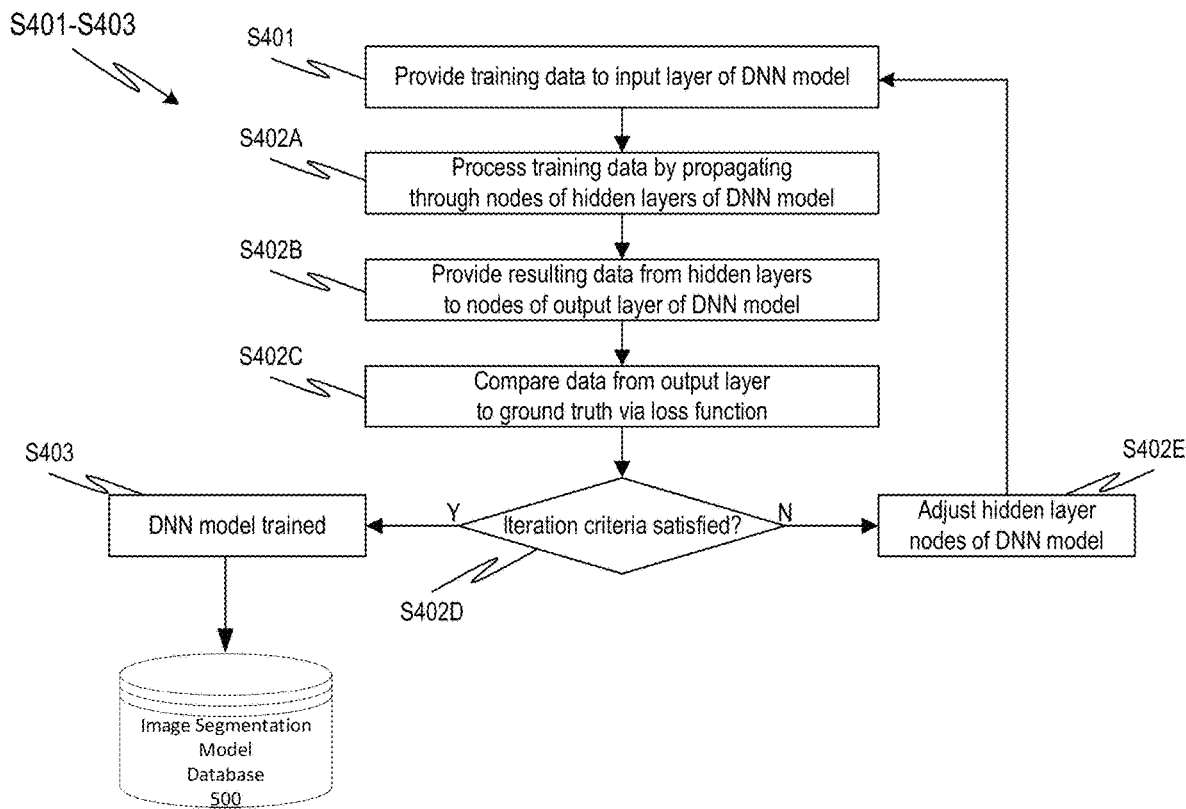
FIG. 16 is a simplified node map of a deep neural network (DNN), according to various embodiments of the disclosed subject matter.
Figure 17:
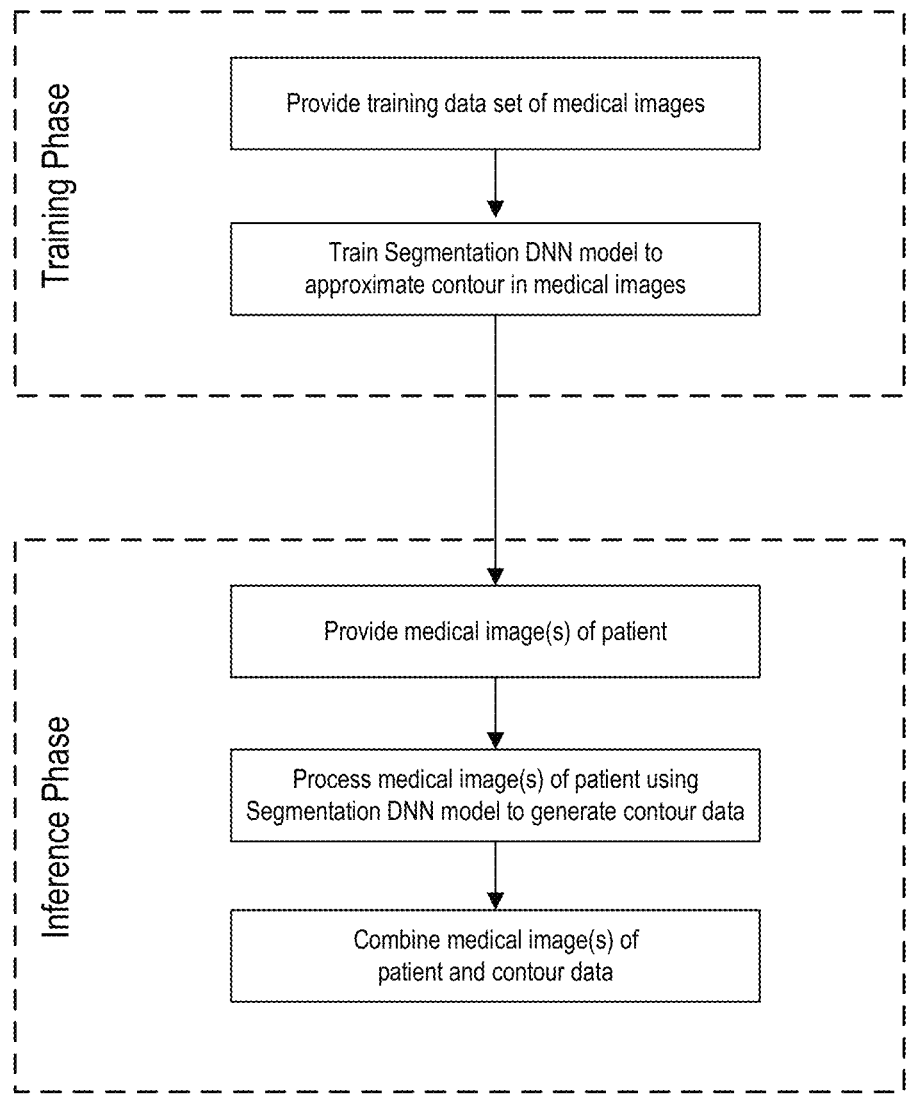
FIG. 17 is a simplified schematic diagram illustrating of the training and inference stages of a deep learning based segmentation model, according to various embodiments of the disclosed subject matter.

FIG. 16 illustrate exemplary process steps S402A-S402E included in the training step S402 of FIG. 14. For example, in step S402A, the training data supplied in S401 is propagated through the nodes of hidden layers of an input DNN model. The resulting data from the hidden layer are provided to nodes of the output layer of the DNN mode in S402B. In step S402C, the data from the output layer is compared with the ground truth via a loss function. For example, loss function can be mean-squared error, dice loss, cross entropy-based losses or any other loss function known in the art.

During the training S402, the DNN model is given feedback by loss function on how well its output matches the correct output. Once an iteration criteria is satisfied at S402D (e.g., loss function meets a predetermined threshold, a threshold number of iterations has been reached, or no further improvement is seen between iterations), the DNN model is fixed at S403. Otherwise, the training S402 proceeds to S402E, where the DNN model is modified, e.g., by adjusting parameters of the hidden layer nodes, in order to improve the match between output and the desired output.

The training process S402 can iterate repeatedly until the desired iteration criteria is met at S402D. The DNN model is then considered trained and the trained DNN model of S403 can be stored in the image segmentation model database 500.

A plurality of DNN models can be trained in accordance with this process.

To generate a plurality of shape or statistical shape models, contours of different anatomical structures can be manually, automatically or semi-automatically generated in step S502 based on training data set of medical image provided in S401 from the image database 400 or 401, and in S503, statistical models generated, each mathematically describing the shape and/or appearance of so obtained contours.

To generate a plurality of machine learning based segmentation models, in S602 feature vectors are extracted from training image data provided in S601 from image database 400 or 401, to be used to train an input machine learning model in S603. The trained machine learning models of S604 can then be stored in the image segmentation model database 500.

Although a library of different segmentation models can be generated using any of the disclosed and any other suitable methods, the image segmentation model database 500 may also be a database 500 that includes a library of previously compiled trained automatic segmentation models that are accessible to different user/systems/frameworks/platforms, such as those described herein. The image segmentation model database 500 may also include a library of parameters corresponding to each of the previously compiled trained automatic segmentation models.

Various modifications to the layout and processes illustrated in FIGS. 10-16 are also possible according to one or more contemplated embodiments. For example, the algorithm-modified contour data obtained from the inference engines 315A-315N could be combined with the original medical image(s), such that the contours are overlaid on the corresponding anatomical structures in the image, for example, for visualization by user or use in radiation treatment planning. Alternatively, the segmentation models in inference engines 315A-315 may directly produce the contours on the medical images as an output, and the algorithms can directly modify the contours on the medical images, without necessarily requiring a separate combination step.

It will be appreciated that a network-based system for automatic multi-structure image segmentation using different segmentation models is disclosed, comprising at least one processing device configured to access, via the network, a library of different image segmentation models; select and apply all or a subset of the image segmentation models to be used to contour one or more anatomical structures selected by a user via a user interface; and combine results of different segmentation model outcomes.

It will also be appreciated that a network-based system for automatic image segmentation the system is disclosed, comprising a memory having instructions thereon, wherein when executed, the instructions cause the processor to: access a database including one or more medical images associated with a patient, the medical images including one or more anatomical structures of the patient; access a database including the library of different image segmentation models; and upon a request by the user via the user interface to contour one or more anatomical structures on one or more of the medical images: determine which ones of the segmentation models in the database support segmentation of at least one of the one or more anatomical structures desired to be contoured; display to the user, on a selection screen, a list of the image segmentation models determined to support segmentation of one or more of the desired anatomical structures, and a list of the anatomical structures that each of the determined segmentation models supports; for each anatomical structure desired to be contoured, allow the user to select one or more segmentation models from the displayed list to be used; apply the selected segmentation models to generate corresponding contours for the desired anatomical structures; and display the generated contours on the one or more images for user review.

It will also be appreciated that a network-based automatic segmentation method is disclosed, comprising: inputting by a user via a user interface a list of anatomical structures desired to be contoured; automatically generating and displaying on a selection screen of the user interface a list of available segmentation models suitable to contour at least one of the desired anatomical structures, and a list of anatomical structures each available segmentation model supports; for each desired anatomical structure, allowing the user to select one or more of the displayed segmentation models to be used for contouring; applying the selected segmentation models; and displaying the segmentation results to the user for review, wherein, upon determination by the user that one or more of the segmentation results are not acceptable, allowing the user to return to the selection screen and select a different set of segmentation models for contouring.

The automatic generation of the list of suitable segmentation models may include: accessing via the network a database including a plurality of automatic segmentation models and corresponding anatomical structures each of the segmentation models supports; determining which ones of the automatic segmentation models in the database support segmentation of at least one of the desired anatomical structures; and selecting for display to the user each of the segmentation models from the database that support segmentation of at least one of the desired anatomical structures.

The applying the selected segmentation models may include: accessing via the network the selected segmentation models; and for each desired anatomical structure, applying the selected one or more segmentation models to generate one or more contours.

The segmentation models can be applied in a consecutive fashion.

The segmentation models can be applied in a simultaneous fashion.

The displaying may include displaying the generated contours on one or more input images.

The input images can be images accessed via the network from a database upon user request.

The method may further comprise allowing the user to combine the segmentation results.

The combining can be done on a weighted basis or using Boolean operations.

The combining can be done manually.

The combining may include combining the contours obtained for the same anatomical structure using different segmentation models.

The combining may include combining the contours obtained for different anatomical structures using different segmentation models.

The method may further comprise processing the generated contours prior to display to the user.

The processing may include automatically modifying the generated contours by modifying the margins of the anatomical structures.

The processing may include automatically rejecting specific contours.

The specific contours may include contours of predefined planes of one or more of the desired anatomical structures.

The method may further comprise allowing the user to further process the generated contours.

The further processing may include modifying the generated contours.

The modifying may include cutting one or more of the generated contours at predefined locations.

The method may further comprise automatically locating the predefined locations.

The available image segmentation models in the database can include segmentation models based on deep learning, segmentation models based on atlas, segmentation models based on shape or appearance statistical models, and machine learning based segmentation models.

The desired anatomical structures may include at least one of organs, tissues, bones, and blood vessels.

The database may further include model data associated with each of the segmentation models.

The model data may include one or more of a list of anatomical structures each segmentation model supports, type of protocol each anatomical structure on the list uses for contouring, and input data that each segmentation model needs to perform segmentation.

The input data can include one or more of the type of images the segmentation model requires to perform segmentation, and guidance markers.

The method may further comprise developing a treatment plan for radiotherapy based on the generated contours.

It will also be appreciated that a non-transitory computer-readable storage medium is also disclosed upon which is embodied a sequence of programmed instructions, and a computer processing system that executes the sequence of programmed instructions embodied on the computer-readable storage medium to cause the computer processing system to execute any one or a combination of the herein described method steps, using a system as described herein.

It will be appreciated that the aspects of the disclosed subject matter can be implemented, fully or partially, in hardware, hardware programmed by software, software instruction stored on a computer readable medium (e.g., a non-transitory computer readable medium), or any combination of the above. For example, components of the disclosed subject matter, including components such as a controller, module, model, neural network, or any other feature, can include, but are not limited to, a personal computer or workstation or other such computing system that includes a processor (e.g., graphics processing unit), microprocessor, microcontroller device, or is comprised of control logic including integrated circuits such as, for example, an application specific integrated circuit (ASIC). Features discussed herein can be performed on a single or distributed processor (single and/or multi-core), by components distributed across multiple computers or systems, or by components co-located in a single processor or system. For example, aspects of the disclosed subject matter can be implemented via a programmed general purpose computer, an integrated circuit device (e.g., ASIC), a digital signal processor (DSP), an electronic device programmed with microcode (e.g., a microprocessor or microcontroller), a hard-wired electronic or logic circuit, a programmable logic circuit (e.g., programmable logic device (PLD), programmable logic array (PLA), field-programmable gate array (FPGA), programmable array logic (PAL)), software stored on a computer-readable medium or signal, an optical computing device, a networked system of electronic and/or optical devices, a special purpose computing device, a semiconductor chip, a software module or object stored on a computer-readable medium or signal.

When implemented in software, functions may be stored on or transmitted over as one or more instructions or code on a computer-readable medium. The steps of any process, method, or algorithm disclosed herein may be embodied in a processor-executable software module, which may reside on a computer-readable medium. Instructions can be compiled from source code instructions provided in accordance with a programming language. The sequence of programmed instructions and data associated therewith can be stored in a computer-readable medium (e.g., a non-transitory computer readable medium), such as a computer memory or storage device, which can be any suitable memory apparatus, such as, but not limited to read-only memory (ROM), programmable read-only memory (PROM), electrically erasable programmable read-only memory (EEPROM), random-access memory (RAM), flash memory, disk drive, etc.

As used herein, computer-readable media includes both computer storage media and communication media, including any medium that facilitates transfer of a computer program from one place to another. Thus, a storage media may be any available media that may be accessed by a computer. By way of example, and not limitation, such computer-readable media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer.

Also, any connection is properly termed a computer-readable medium. For example, if the software is transmitted from a website, server, or other remote source using a transmission medium (e.g., coaxial cable, fiber optic cable, twisted pair, digital subscriber line (DSL), or wireless technologies such as infrared, radio, and microwave), then the transmission medium is included in the definition of computer-readable medium. Moreover, the operations of any process, method, or algorithm disclosed herein may reside as one of (or any combination of) or a set of codes and/or instructions on a machine readable medium and/or computer-readable medium, which may be incorporated into a computer program product.

One of ordinary skill in the art will readily appreciate that the above description is not exhaustive, and that aspects of the disclosed subject matter may be implemented other than as specifically disclosed above. Indeed, embodiments of the disclosed subject matter can be implemented in hardware and/or software using any known or later developed systems, structures, devices, and/or software by those of ordinary skill in the applicable art from the functional description provided herein.

In this application, unless specifically stated otherwise, the use of the singular includes the plural, and the separate use of "or" and "and" includes the other, i.e., "and/or." Furthermore, use of the terms "including" or "having," as well as other forms such as "includes," "included," "has," or "had," are intended to have the same effect as "comprising" and thus should not be understood as limiting.

Any range described herein will be understood to include the endpoints and all values between the endpoints. Whenever "substantially," "approximately," "essentially," "near," or similar language is used in combination with a specific value, variations up to and including 10% of that value are intended, unless explicitly stated otherwise.

Many alternatives, modifications, and variations are enabled by the present disclosure.

While specific examples have been shown and described in detail to illustrate the application of the principles of the present invention, it will be understood that the invention may be embodied otherwise without departing from such principles. For example, disclosed features may be combined, rearranged, omitted, etc. to produce additional embodiments, while certain disclosed features may sometimes be used to advantage without a corresponding use of other features. Accordingly, Applicant intends to embrace all such alternative, modifications, equivalents, and variations that are within the spirit and scope of the present invention.

The invention claimed is:

1. A network-based system for automatic image segmentation, comprising:
a processor configured to:
   display to a user on a selection screen a list of anatomical structures associated with one or more images of a patient;
   allow the user to select from the list one or more anatomical structures desired to be contoured;
   access, via the network, a library of different image segmentation models;
   determine the image segmentation models in the library that support segmentation of the one or more anatomical models selected by the user;
   display to the user, a list of the image segmentation models determined to support segmentation of the one or more selected anatomical structures;
   display to the user a list of anatomical structures that each of the determined segmentation models supports;
   allow the user to select all or a subset of the image segmentation models from the list of segmentation models to be used to contour each of the one or more anatomical structures selected by the user;
   apply the selected segmentation models on the selected anatomical structures; and
   combine results of different segmentation model outcomes.

2. The system of claim 1, further comprising:
a memory having instructions thereon, wherein when executed, the instructions cause the processor to:
   access a database including the one or more medical images associated with the patient;
   access a database including the library of different image segmentation models; and
   upon a request by the user via a user interface to contour the one or more anatomical structures on the one or more of the medical images:
      determine which ones of the segmentation models in the database support segmentation of at least one of the one or more anatomical structures desired to be contoured;
      display to the user, on a selection screen, the list of the image segmentation models determined to support segmentation of the one or more of the desired anatomical structures, and the list of the anatomical structures that each of the determined segmentation models supports;
      for each of the anatomical structure desired to be contoured, allow the user to select the one or more segmentation models from the list of the anatomical structures displayed to the user;

apply the one or more selected segmentation models to generate corresponding contours for the desired anatomical structures; and display the generated contours on the one or more images for user review.

3. The system of claim 2, wherein the processor is further configured to allow the user to accept or reject any of the generated contours.

4. The system of claim 3, wherein the processor is further configured to allow the user to combine the contours obtained for the same anatomical structure using different segmentation models.

5. The system of claim 4, wherein the processor is further configured to allow the user to combine the contours obtained for different anatomical structures using different segmentation models.

6. The system of claim 5, wherein the combining is done on a weighted basis.

7. The system of claim 5, wherein the combining is done using Boolean operations.

8. The system of claim 5, wherein the combining is done manually.

9. The system of claim 3, wherein the processor is further configured to allow the user to return to the selection screen and select a different set of segmentation models from the displayed list to generate the contours.

10. The system of claim 2, wherein the processor is configured to further process the generated contours prior to user review.

11. The system of claim 10, wherein the further processing includes automatically modifying margins of the one or more anatomical structures.

12. The system of claim 11, wherein the further processing includes automatically rejecting selected contours.

13. The system of claim 12, wherein the selected contours include contours of predefined planes of the one or more desired anatomical structures.

14. The system of claim 10, wherein the processor is further configured to allow the user to further process the generated contours after review, wherein the further processing includes modifying the generated contours.

15. The system of claim 14, wherein the modifying includes cutting one or more of the generated contours at predefined locations.

16. The system of claim 15, wherein the processor is further configured to locate the predefined locations.

17. The system of claim 2, wherein the database including the segmentation models also includes model data associated with each of the segmentation models, wherein the model data includes one or more of a list of anatomical structures each segmentation model supports, type of protocol each anatomical structure on the list uses for contouring, and input data that each segmentation model requires to perform segmentation, wherein the input data includes one or more of the type of images the segmentation model requires to perform segmentation, and guidance markers.

18. The system of claim 2, further comprising:
a radiotherapy device configured to deliver radiation treatment to a patient,
wherein the processor is further configured to control the radiotherapy device to irradiate the patient according to a treatment plan based at least on the one or more medical images of the patient and the generated contours.

19. The system of claim 1, wherein the library of image segmentation models includes segmentation models based on deep learning, and one or more of segmentation models based on atlas, segmentation models based on shape or appearance statistical models, and machine learning based segmentation models.

20. The system of claim 1, wherein the anatomical structures include one or more of organs, tissues, bones, and blood vessels.

* * * * *